(12) United States Patent
Limoli et al.

(10) Patent No.: US 12,376,805 B2
(45) Date of Patent: Aug. 5, 2025

(54) MOBILE CT IMAGING SYSTEM COMPRISING A MOBILE CT IMAGING MACHINE WITH AN ON-BOARD MOTORIZED BED AND/OR AN ON-BOARD ULTRASOUND IMAGER

(71) Applicant: NeuroLogica Corporation, a subsidiary of Samsung Electronics Co., Ltd., Danvers, MA (US)

(72) Inventors: Michael Limoli, Merrimac, MA (US); Richard DeSalvo, Danvers, MA (US); Alexander Drosos, Lowell, MA (US)

(73) Assignee: NeuroLogica Corporation, a subsidiary of Samsung Electronics Co., Ltd., Danvers, MA (US)

( * ) Notice: Subject to any disclaimer, the term of this patent is extended or adjusted under 35 U.S.C. 154(b) by 84 days.

(21) Appl. No.: 18/081,082

(22) Filed: Dec. 14, 2022

(65) Prior Publication Data
US 2023/0181127 A1    Jun. 15, 2023

Related U.S. Application Data

(60) Provisional application No. 63/289,426, filed on Dec. 14, 2021.

(51) Int. Cl.
*A61B 6/04* (2006.01)
*A61B 6/00* (2006.01)
(Continued)

(52) U.S. Cl.
CPC ............ *A61B 6/035* (2013.01); *A61B 6/0407* (2013.01); *A61B 6/0487* (2020.08);
(Continued)

(58) Field of Classification Search
CPC ..... A61B 6/035; A61B 6/0407; A61B 6/0487; A61B 6/4405; A61B 6/4417; A61B 6/461;
(Continued)

(56) References Cited

U.S. PATENT DOCUMENTS 5,034,970 A * 7/1991 Yahata ................ A61B 6/0487
378/68
8,888,364 B2   11/2014 Bailey et al.
(Continued)

FOREIGN PATENT DOCUMENTS

JP       2009543670 A *  7/2007 ............. A61B 8/481
WO     WO 2017/180569       10/2017

OTHER PUBLICATIONS

グリフィス Integrated Medical Imaging System Machine Translation JP2009543670 accessed Jul. 26, 2024 (Year: 2024).*

*Primary Examiner* — Anne M Kozak
*Assistant Examiner* — Brooke Lyn Klein
(74) *Attorney, Agent, or Firm* — Pandiscio & Pandiscio

(57) ABSTRACT

An imaging system for imaging an object, the imaging system comprising: an imaging unit comprising a housing having a center opening for receiving the object to be imaged; and a patient support for supporting the object to be imaged, the patient support being pivotally mounted to the housing, wherein the patient support is configured to pivot between (i) a first, folded configuration in which the patient support is disposed close to the housing, whereby to facilitate transport of the imaging unit, and (ii) a second, unfolded configuration in which the patient support is aligned with the center opening, whereby to facilitate imaging of the object on the patient support.

15 Claims, 23 Drawing Sheets

(51) Int. Cl.
  *A61B 6/03*    (2006.01)
  *A61B 6/46*    (2024.01)
(52) U.S. Cl.
  CPC .......... *A61B 6/4405* (2013.01); *A61B 6/4417* (2013.01); *A61B 6/461* (2013.01)
(58) Field of Classification Search
  CPC ... A61B 6/032; A61B 6/03–035; A61B 6/481; A61G 13/00–1295
  See application file for complete search history.

(56) References Cited

U.S. PATENT DOCUMENTS

| | | |
|---|---|---|
| 9,986,954 B2 * | 6/2018 | Bailey .................. A61B 6/0407 |
| 10,039,505 B2 | 8/2018 | Bailey et al. |
| 10,617,375 B2 | 4/2020 | Bailey et al. |
| 10,687,770 B2 | 6/2020 | Sullivan et al. |
| 11,903,749 B2 | 2/2024 | Zilberstien et al. |
| 2007/0167806 A1 * | 7/2007 | Wood ...................... A61B 6/032 |
| | | 600/459 |
| 2013/0305452 A1 * | 11/2013 | Zhongqiang ........... A61B 6/032 |
| | | 5/601 |
| 2020/0205756 A1 | 7/2020 | Bailey et al. |
| 2020/0367842 A1 | 11/2020 | Limoli et al. |
| 2021/0045712 A1 * | 2/2021 | de Jonge ............. A61B 8/4411 |

\* cited by examiner

MOBILE CT IMAGING SYSTEM COMPRISING A MOBILE CT IMAGING MACHINE WITH AN ON-BOARD MOTORIZED BED AND/OR AN ON-BOARD ULTRASOUND IMAGER

REFERENCE TO PENDING PRIOR PATENT APPLICATION

This patent application claims benefit of prior U.S. Provisional Patent Application Ser. No. 63/289,426, filed Dec. 14, 2021 by Neurologica Corporation, a subsidiary of Samsung Electronics Co., Ltd. and Michael Limoli et al. for MOBILE CT IMAGING SYSTEM COMPRISING A MOBILE CT IMAGING MACHINE WITH AN ON-BOARD MOTORIZED BED AND/OR AN ON-BOARD ULTRASOUND IMAGER.

The above-identified patent application is hereby incorporated herein by reference.

FIELD OF THE INVENTION

This invention relates to imaging systems in general, and more particularly to mobile anatomical imaging systems.

BACKGROUND OF THE INVENTION

Computerized Tomography (CT)

In many situations it can be desirable to image the interior of opaque objects. By way of example but not limitation, in the medical field, it can be desirable to image the interior of a patient's body so as to allow viewing of internal structures without physically penetrating the skin of the patient.

Computerized Tomography (CT) has emerged as a key imaging modality in the medical field. CT imaging machines generally operate by directing X-rays into the body from a variety of positions, detecting the X-rays passing through the body, and then processing the detected X-rays so as to build a three-dimensional (3D) data set of the patient's anatomy. This 3D data set can then be processed so as to create a 3D computer model of the patient's anatomy. The 3D data set and 3D computer model can then be visualized so as to provide images (e.g., slice images, 3D computer images, etc.) of the patient's anatomy.

By way of example but not limitation, and looking now at FIGS. 1 and 2, there is shown an exemplary CT imaging machine 5. CT imaging machine 5 generally comprises a torus 10 which is supported by a base 15. A center opening 20 is formed in torus 10. Center opening 20 receives the patient anatomy which is to be scanned.

Looking next at FIG. 3, torus 10 generally comprises a fixed gantry 22, a rotating disc 23, an X-ray tube assembly 25 and an X-ray detector assembly 30. More particularly, fixed gantry 22 is disposed concentrically about center opening 20. Rotating disc 23 is rotatably mounted to fixed gantry 22. X-ray tube assembly 25 and X-ray detector assembly 30 are mounted to rotating disc 23 in diametrically-opposing relation, such that an X-ray beam 40 (generated by X-ray tube assembly 25 and detected by X-ray detector assembly 30) is passed through the patient anatomy disposed in center opening 20. Inasmuch as X-ray tube assembly 25 and X-ray detector assembly 30 are mounted on rotating disc 23 so that they are rotated concentrically about center opening 20, X-ray beam 40 will be passed through the patient's anatomy along a full range of radial positions, so as to enable CT imaging machine 5 to create a "slice" image of the anatomy penetrated by the X-ray beam. Furthermore, by moving the patient and CT imaging machine 5 relative to one another during scanning, a series of slice images can be acquired, and thereafter appropriately processed, so as to create a 3D data set of the scanned anatomy. This 3D data set can then be processed so as to create a 3D computer model of the scanned anatomy. It is common to configure X-ray detector assembly 30 so that multiple slices of images (e.g., 8 slices, 16 slices, 32 slices, etc.) may be acquired with each rotation of rotating disc 23, whereby to speed up the acquisition of scan data.

In practice, it is now common to effect helical scanning of the patient's anatomy so as to generate a 3D data set of the scanned anatomy, which can then be processed so as to create a 3D computer model of the scanned anatomy. The 3D data set and 3D computer model can then be visualized so as to provide images (e.g., slice images, 3D computer images, etc.) of the patient's anatomy.

The various electronic hardware and software for controlling the operation of rotating disc 23, X-ray tube assembly 25 and X-ray detector assembly 30, as well as for processing the acquired scan data so as to generate the desired slice images, 3D data set and 3D computer model, may be of the sort well known in the art and may be located in torus 10 and/or base 15.

The images produced by CT imaging machine 5 may be viewed on a display screen 41 provided on CT imaging machine 5 or on a remote screen (not shown).

Fixed CT Imaging Machine with Motorized Bed

In many cases, CT imaging machine 5 is intended to be stationary, in which case base 15 of CT imaging machine 5 is set in a fixed position on the floor of a room and a special motorized bed is provided to move the patient relative to CT imaging machine 5 during scanning. More particularly, and looking now at FIG. 4, with a stationary CT imaging machine 5A, the patient is brought to the location of CT imaging machine 5A, the patient is placed on the special motorized bed 42, and then the motorized bed 42 is used to move the patient relative to CT imaging machine 5A (i.e., to advance the patient into center opening 20 of CT imaging machine 5A) so that some or all of the length of the patient may be scanned by CT imaging machine 5A. Note that motorized bed 42 typically comprises a pedestal 44 and a patient support 46, with pedestal 44 being fixed in place relative to the stationary CT imaging machine 5A and the patient support 46 moving relative to pedestal 44 (and relative to stationary CT imaging machine 5A). Note also that patient support 46 is typically formed out of a radiolucent material so as to not interfere with CT imaging of the patient.

Mobile CT Imaging Machine

In other cases, CT imaging machine 5 is intended to be mobile so that the CT imaging machine may be brought to the patient and the patient scanned at the patient's current location, with the CT imaging machine moving relative to the patient during scanning. Scanning the patient with a mobile CT imaging machine 5 can be highly advantageous, since it can reduce delays in patient scanning (e.g., the patient can be scanned in an emergency room rather than waiting to be transported to the radiology department) and/or it can allow the patient to be scanned without requiring movement of the patient (e.g., the patient can be scanned at their bedside in an intensive care unit, "ICU").

To this end, and looking now at FIGS. 5 and 6, base 15 of a mobile CT imaging machine 5B may comprise a transport assembly 50 for (i) moving mobile CT imaging machine 5B to the location of the patient prior to scanning, and (ii) moving the CT imaging machine 5B relative to the patient during scanning. More particularly, transport assembly 50 preferably comprises (i) a gross movement mechanism 55 for moving CT imaging machine 5B relatively quickly across room distances, so that the CT imaging machine can be quickly and easily brought to the bedside of the patient, such that the patient can be scanned at their bedside without needing to be moved to a radiology department, and (ii) a fine movement mechanism 60 for moving the CT imaging machine precisely, relative to the patient, during scanning so that the patient can be scanned on their bed or gurney without needing to be moved onto a special motorized bed.

In one preferred form of the invention, gross movement mechanism 55 preferably comprises a plurality of free-rolling casters 62, and fine movement mechanism 60 preferably comprises a plurality of centipede belt drives 63 (which can be configured for either stepped or continuous motion, whereby to provide either stepped or continuous scanning of the patient). Hydraulic apparatus 65 permits either gross movement mechanism 55 or fine movement mechanism 60 to be engaged with the floor, whereby to facilitate appropriate movement of mobile CT imaging machine 5B.

Thus, with mobile CT imaging machine 5B, the mobile CT imaging machine may be pre-positioned in an "out of the way" location (e.g., in an unused corner of an emergency room) and then, when a patient requires scanning, the patient may be quickly and easily scanned at their bedside, i.e., by simply moving the mobile CT imaging machine to the patient's bedside on gross movement mechanism 55 (e.g., on casters 62), and thereafter moving the mobile CT imaging machine during scanning on fine movement mechanism 60 (e.g., on centipede belt drives 63).

Note that other mobile CT imaging machines are known in the art.

By way of example but not limitation, and looking now at FIG. 7, there is provided a mobile CT imaging machine 5C which is substantially the same as mobile CT imaging machine 5B, except that (i) gross movement mechanism 55 of mobile CT imaging machine 5B is replaced by gross movement mechanism 55C of mobile CT imaging system 5C, wherein gross movement mechanism 55C comprises a plurality of powered mecanum wheels 70 (also known as "omni" wheels or "ilon" wheels) for providing mobile CT imaging machine 5C with omnidirectional powered movement, and (ii) fine movement mechanism 60 of mobile CT imaging machine 5B is replaced by fine movement mechanism 60C of mobile CT imaging machine 5C, wherein fine movement mechanism 60C comprises a plurality of powered wheels 63C for moving mobile CT imaging machine 5C during scanning. See, for example, U.S. Pat. No. 10,687,770, issued Jun. 23, 1920 to NeuroLogica Corporation, a subsidiary of Samsung Electronics Co., Ltd., for MOBILE ANATOMICAL IMAGING SYSTEM WITH IMPROVED MOVEMENT SYSTEM, which patent is hereby incorporated herein by reference.

By way of further example but not limitation, and looking now at FIG. 8, there is provided a mobile CT imaging machine 5D which is provided with so-called "Liddiard wheels" 76, wherein each Liddiard wheel 76 can be independently rotated (i) about the axis of rotation of powered axle 78, and/or (ii) about its toroidal axis (i.e., orthogonal to the axis of rotation of powered axle 78), whereby to permit mobile CT imaging machine 5D to be moved in any direction (e.g., over long distances when being brought to the patient and over short distances during scanning of the patient). By selectively driving each of the Liddiard wheels 76 in a coordinated fashion, omnidirectional powered movement of mobile CT imaging machine 5D can be achieved. Thus, Liddiard wheels 76 are essentially motorized wheels which, when operated in a coordinated fashion, can provide omnidirectional drive for mobile CT imaging machine 5D, with mobile CT imaging machine 5D being steered by adjusting (i) the direction and rate of rotation of the various powered axles 78, and/or (ii) the direction and rate of rotation of the various tires 79 around their toroidal axes. Significantly, Liddiard wheels 76 can provide omnidirectional drive for mobile CT imaging machine 5D without requiring pivoting (i.e., "steering") of Liddiard wheels 76 relative to mobile CT imaging machine 5D. See, for example, U.S. Pat. No. 11,369,326, issued Jun. 28, 1922 to NeuroLogica Corporation, a subsidiary of Samsung Electronics Co., Ltd., for MOBILE ANATOMICAL IMAGING SYSTEM WITH IMPROVED MOVEMENT SYSTEM COMPRISING LIDDIARD WHEELS, which patent is hereby incorporated herein by reference.

The Need for a Mobile CT Imaging Machine Comprising an On-Board Motorized Bed In some circumstances, the patient may be in a location where a bed is not available, or if a bed is available, the available bed is not radiolucent (and therefore cannot be used to support the patient during scanning). In these circumstances, CT scanning of at least the torso of the patient, and in many cases most of the anatomy of the patient, is not possible. It would, therefore, be desirable to provide a mobile CT imaging machine comprising an on-board motorized bed (i.e., a motorized bed mounted to the CT imaging machine) so that the mobile CT imaging machine and the on-board motorized bed can be moved as a unit to the patient, whereby to permit scanning of the patient without requiring the patient to move to the location of a scanning bed.

Thus, there exists a need for a new and improved mobile CT imaging machine comprising an on-board motorized bed for permitting scanning of the patient wherever the CT machine is located.

The Need for a Mobile CT Imaging Machine Comprising an On-Board Ultrasound Imager In addition to the foregoing, in some circumstances a patient being scanned with a mobile CT imaging machine may also have a condition which is susceptible to being separately scanned with an ultrasound imager. In this case, it may be desirable to scan the patient with an ultrasound imager, rather than with CT, in order to reduce (or eliminate) the radiation exposure of the patient. It would, therefore, be desirable to provide a mobile CT imaging machine comprising an on-board ultrasound imager so that the mobile CT imaging machine and the on-board ultrasound imager can be moved as a single unit to the patient, whereby to permit scanning of the patient using the desired imaging modality (e.g., CT and/or ultrasound).

Thus, there also exists a need for a new and improved mobile CT imaging system comprising an on-board ultrasound imager.

SUMMARY OF THE INVENTION

These and other objects of the present invention are addressed by the provision and use of a new and improved mobile CT imaging system which comprises a mobile CT imaging machine comprising an on-board motorized bed and/or an on-board ultrasound imager.

In one preferred form of the invention, there is provided an imaging system for imaging an object, the imaging system comprising:
an imaging unit comprising a housing having a center opening for receiving the object to be imaged; and
a patient support for supporting the object to be imaged, the patient support being pivotally mounted to the housing, wherein the patient support is configured to pivot between (i) a first, folded configuration in which the patient support is disposed close to the housing, whereby to facilitate transport of the imaging unit, and (ii) a second, unfolded configuration in which the patient support is aligned with the center opening, whereby to facilitate imaging of the object on the patient support.

In another preferred form of the invention, there is provided a method for imaging an object, the method comprising:
providing an imaging system comprising:
an imaging unit comprising a housing having a center opening for receiving the object to be imaged; and
a patient support for supporting the object to be imaged, the patient support being pivotally mounted to the housing, wherein the patient support is configured to pivot between (i) a first, folded configuration in which the patient support is disposed close to the housing, whereby to facilitate transport of the imaging unit, and (ii) a second, unfolded configuration in which the patient support is aligned with the center opening, whereby to facilitate imaging of the object on the patient support;
positioning the patient support in its second, unfolded configuration;
positioning an object on the patient support while the patient support is in its second, unfolded configuration;
moving the object into the central opening; and
imaging the object in the central opening.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
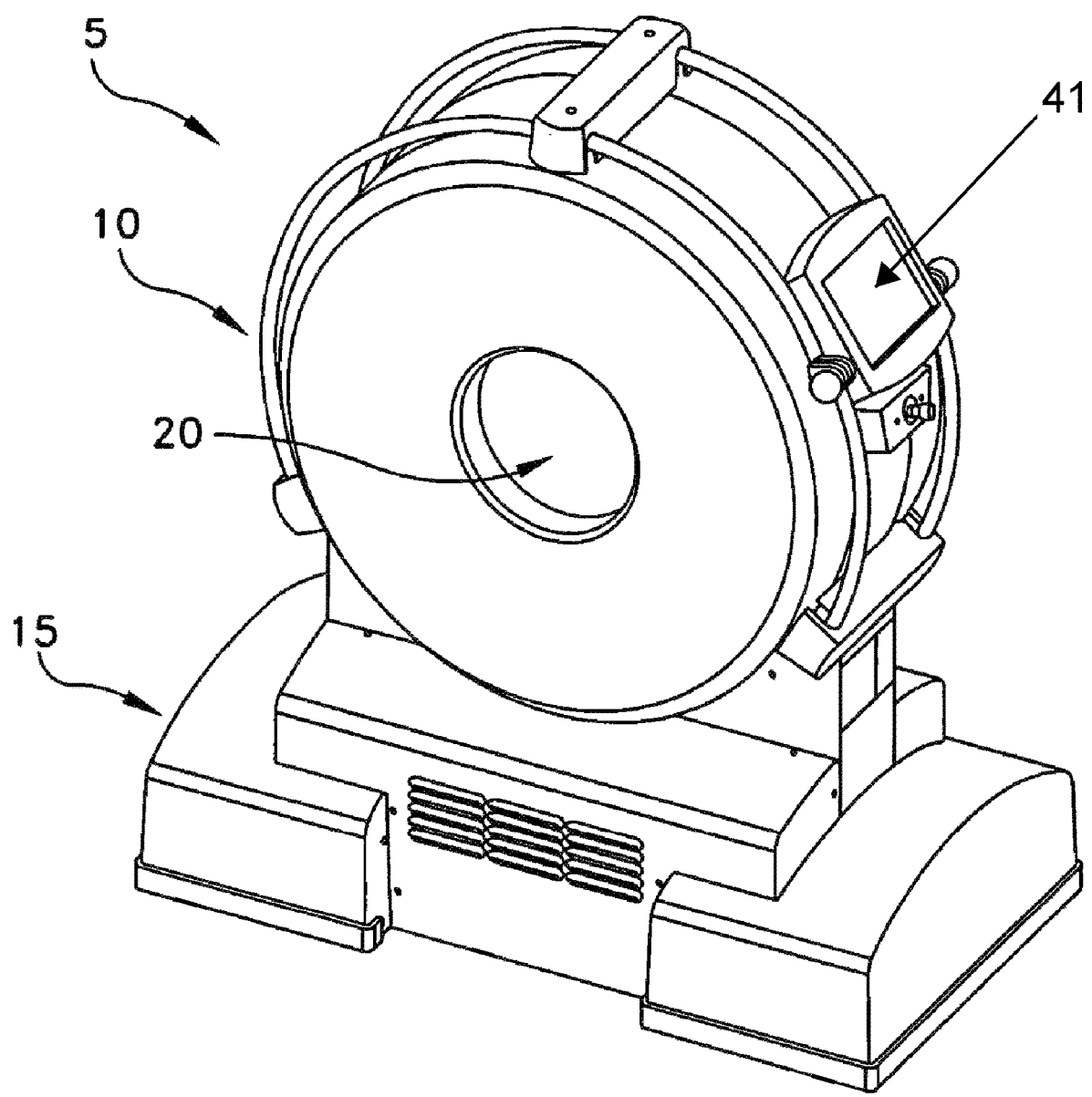
FIGS. 1 and 2 are schematic views showing the exterior of an exemplary CT imaging machine.
Figure 2:
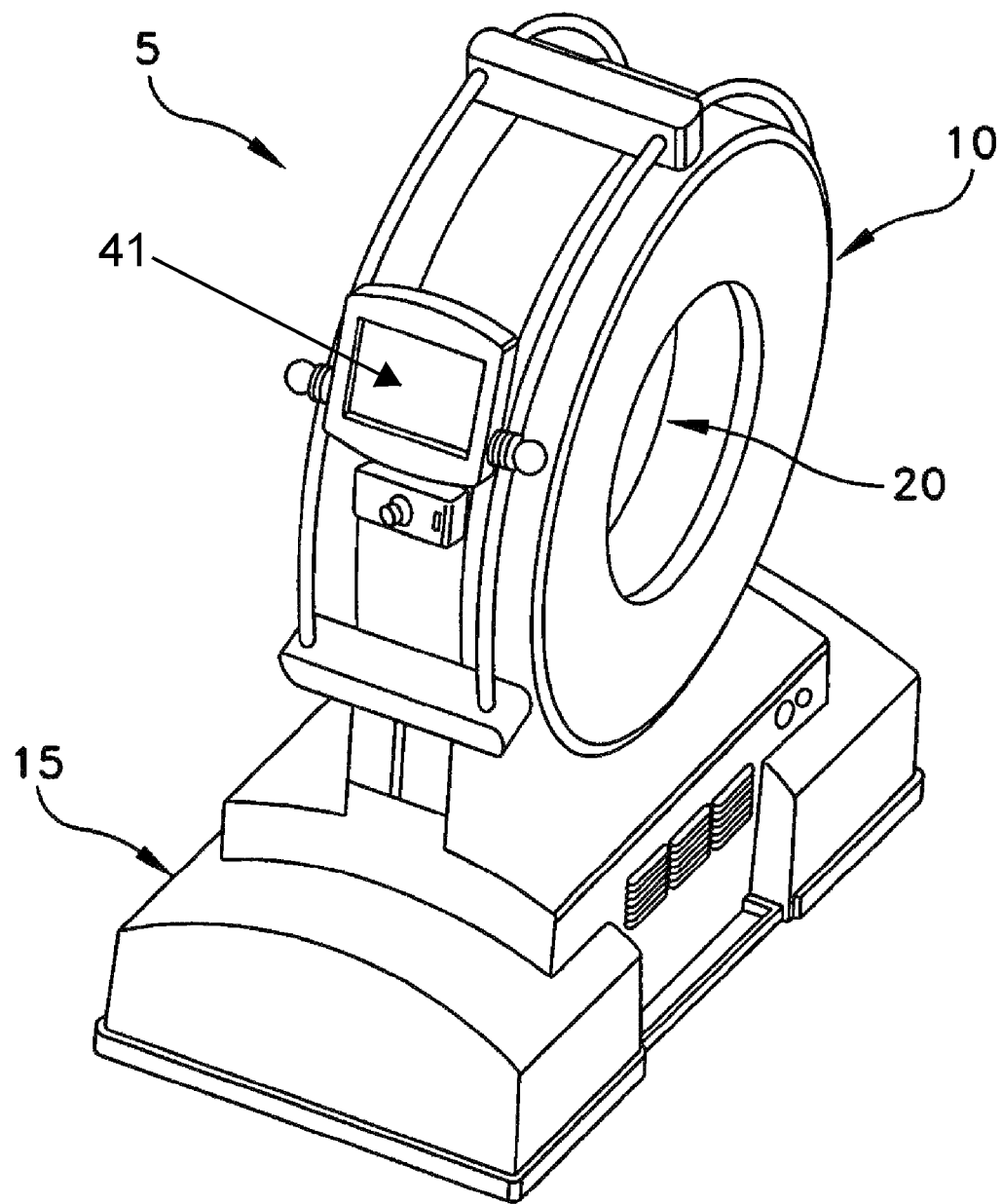
Figure 3:
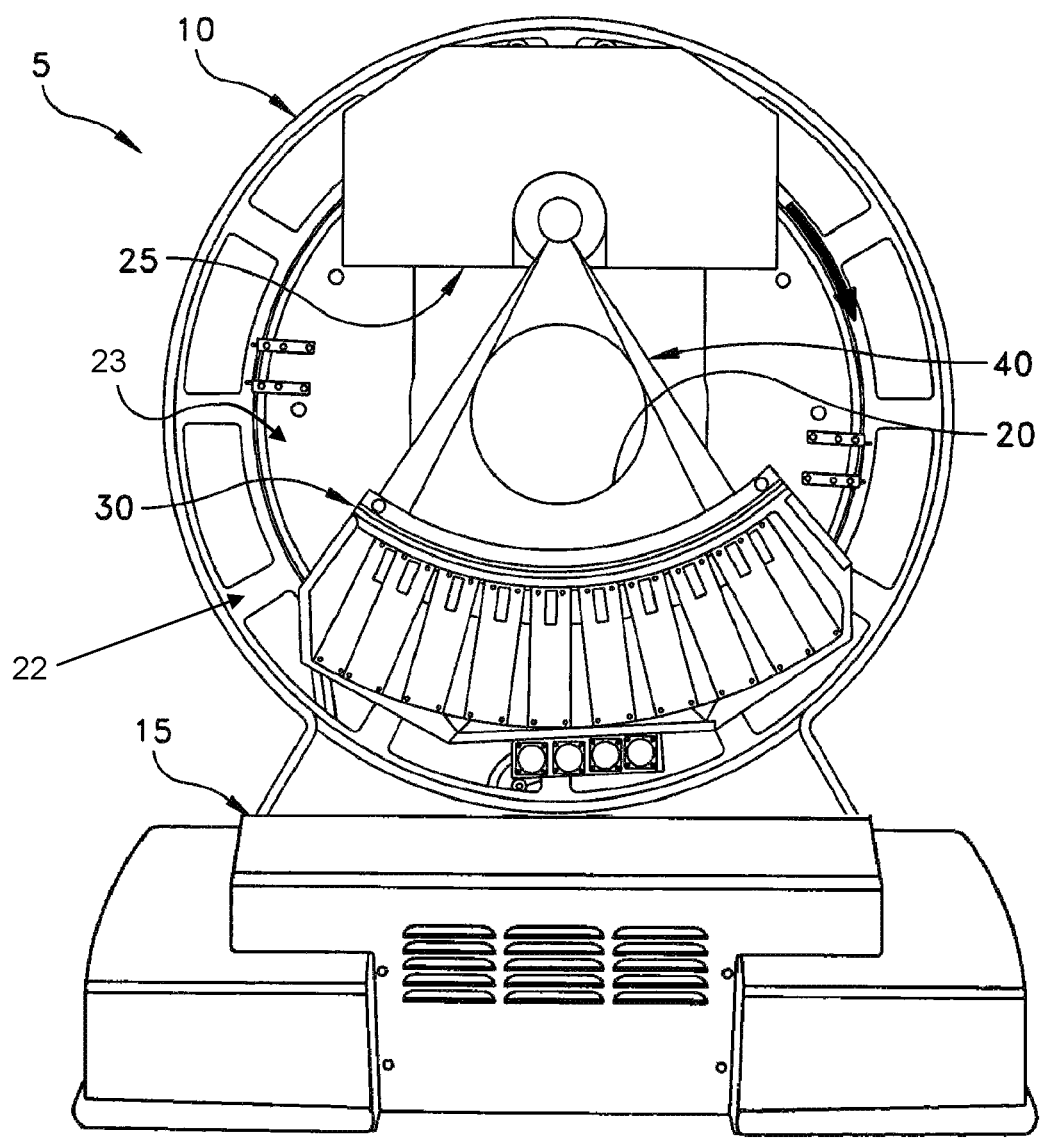
FIG. 3 is a schematic view showing various components in the torus of the exemplary CT imaging machine shown in FIGS. 1 and 2.
Figure 4:
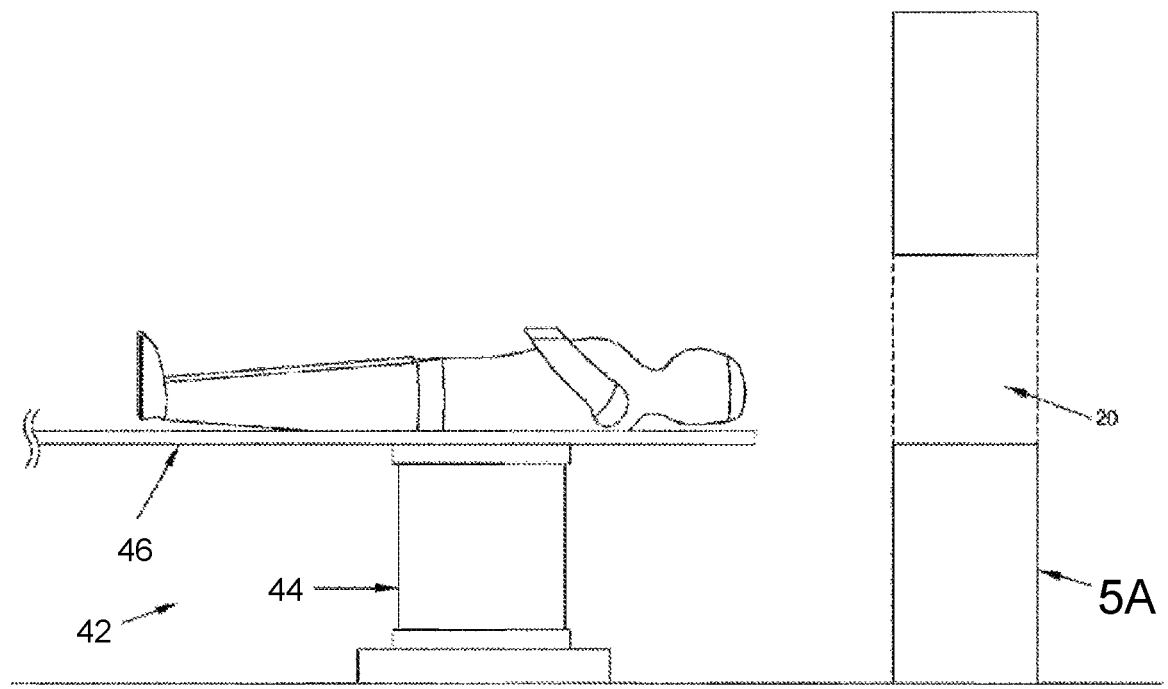
FIG. 4 is a schematic view showing an exemplary fixed CT imaging machine and a motorized bed.
Figure 5:
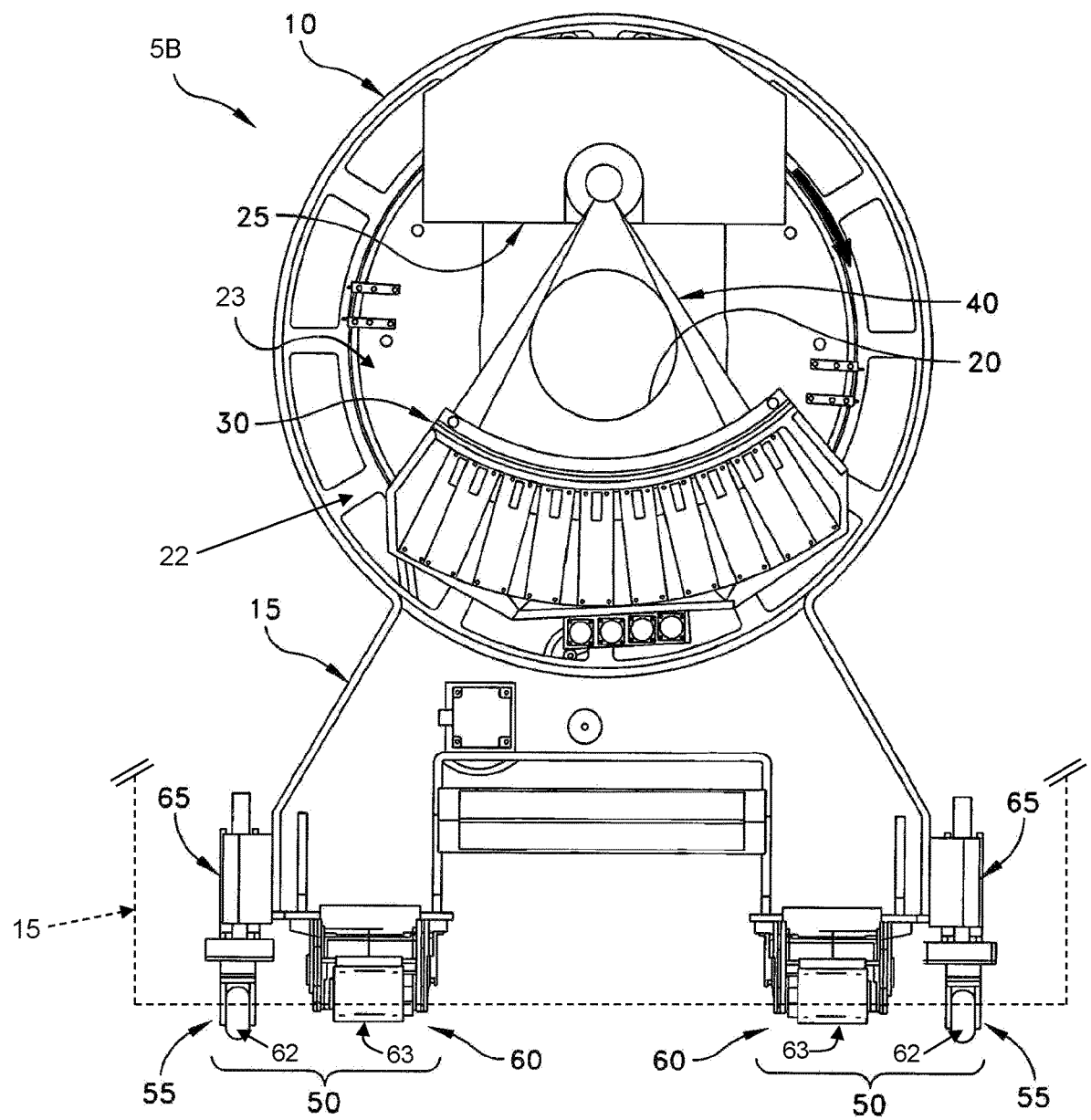
FIGS. 5 and 6 are schematic views showing an exemplary transport assembly for an exemplary mobile CT imaging machine.
Figure 6:
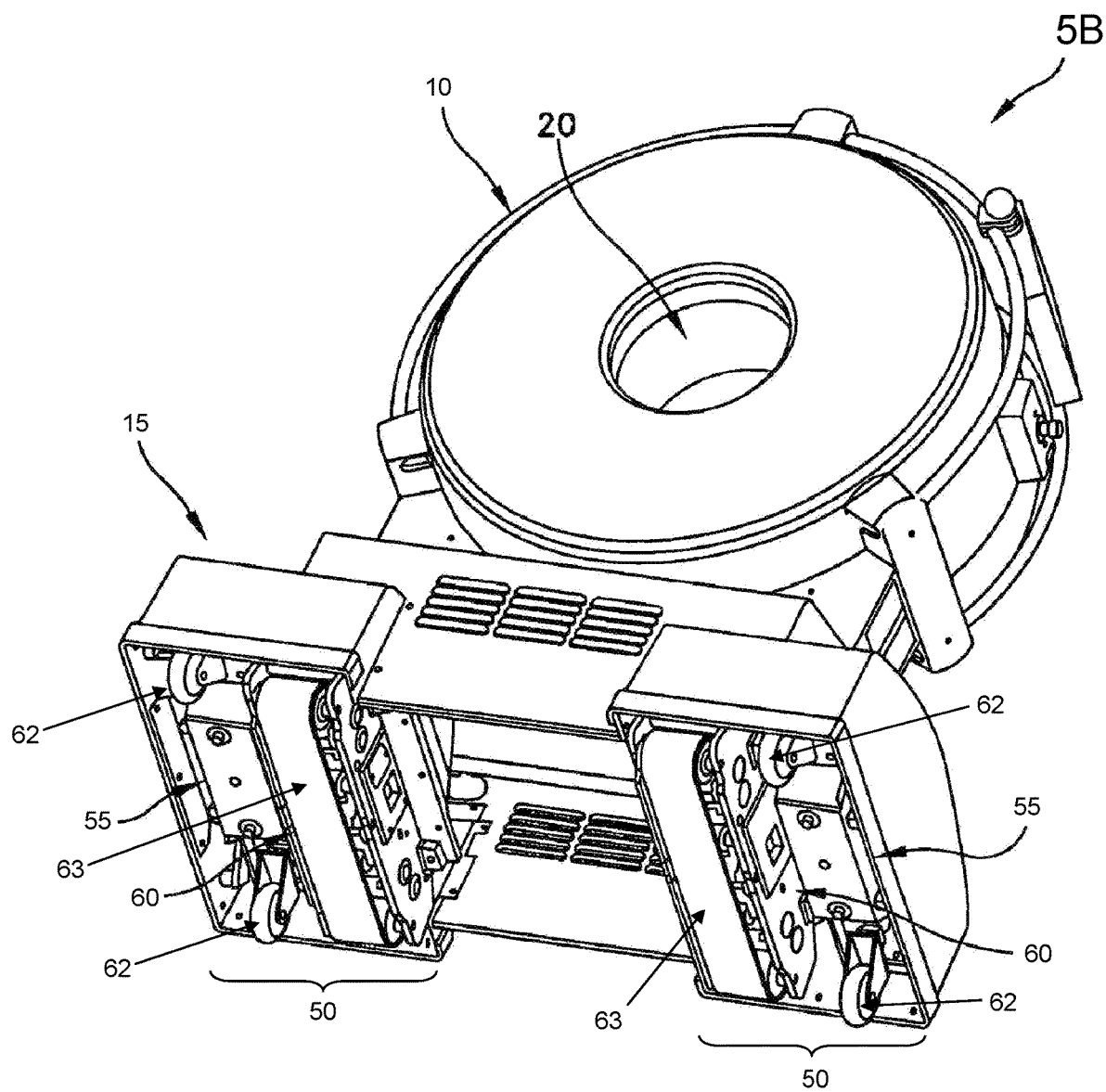
Figure 7:
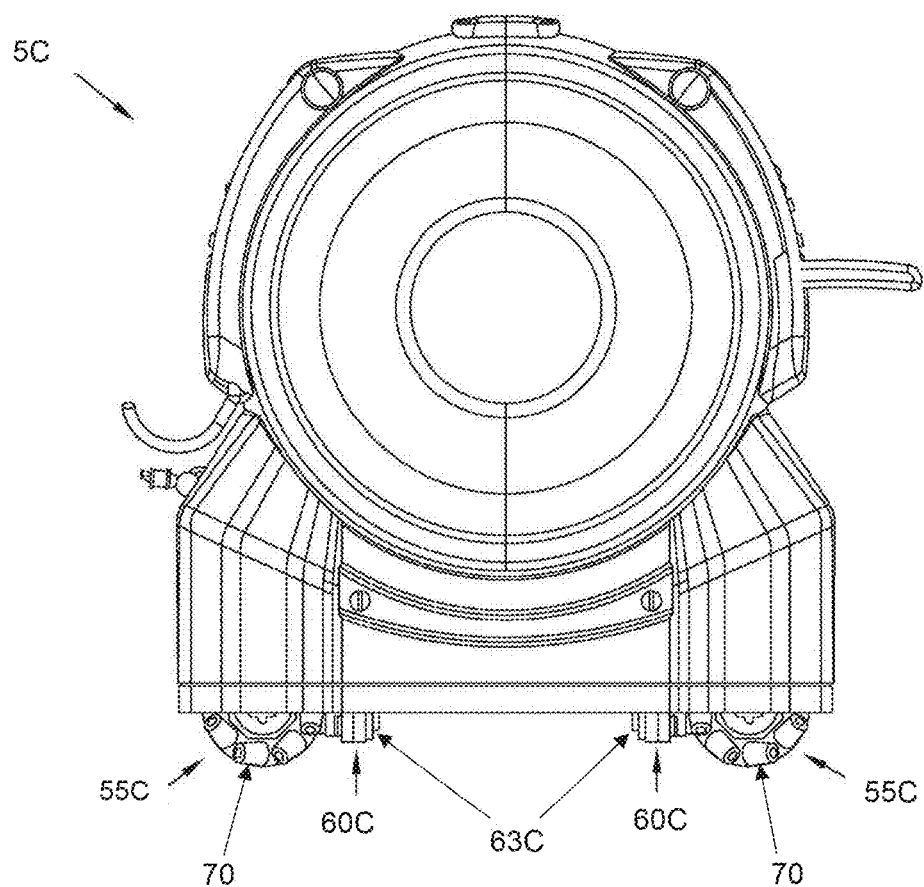
FIG. 7 is a schematic view showing another exemplary transport assembly for an exemplary mobile CT imaging machine.
Figure 8:
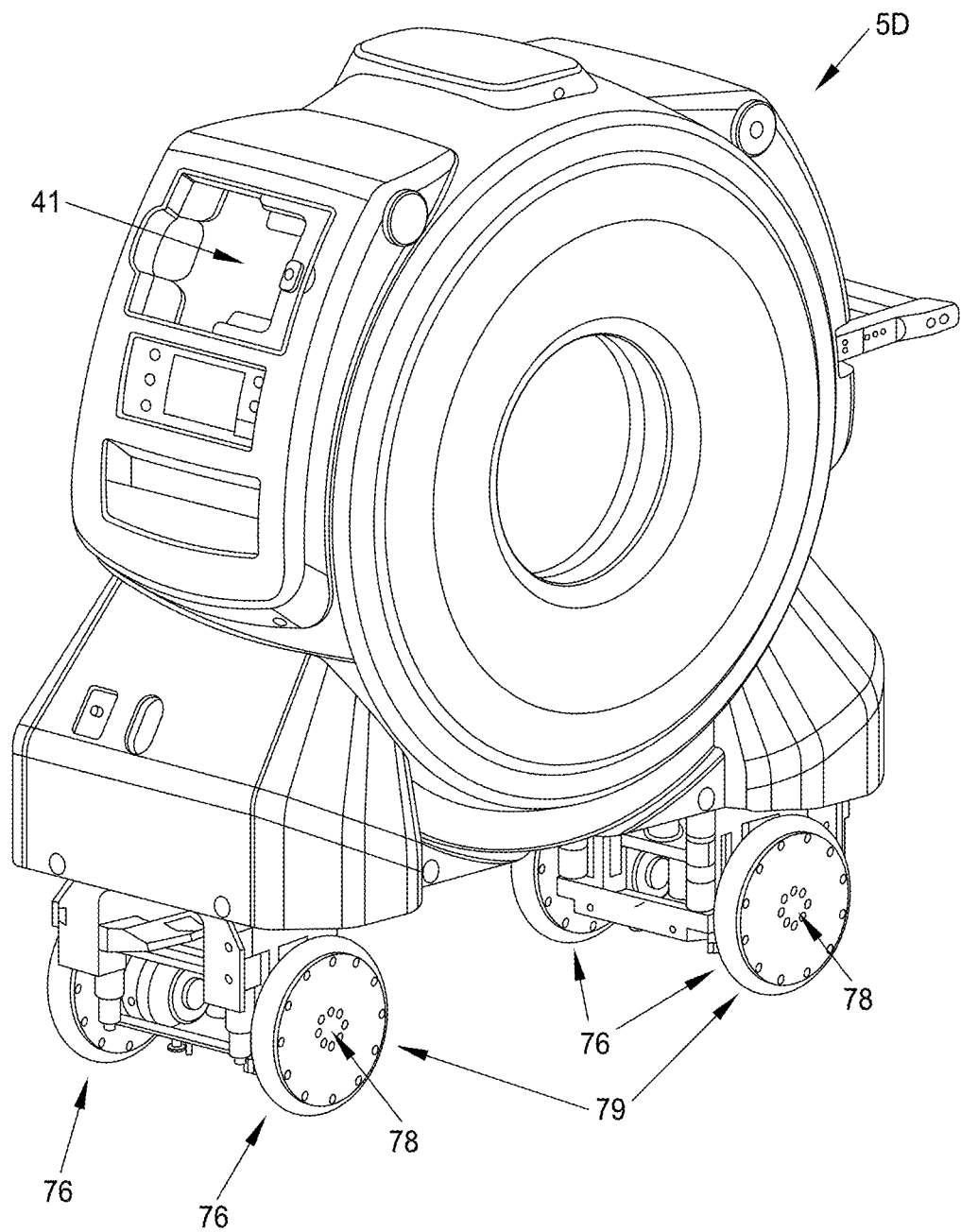
FIG. 8 is a schematic view showing still another exemplary transport assembly for an exemplary mobile CT imaging machine.
Figure 9:
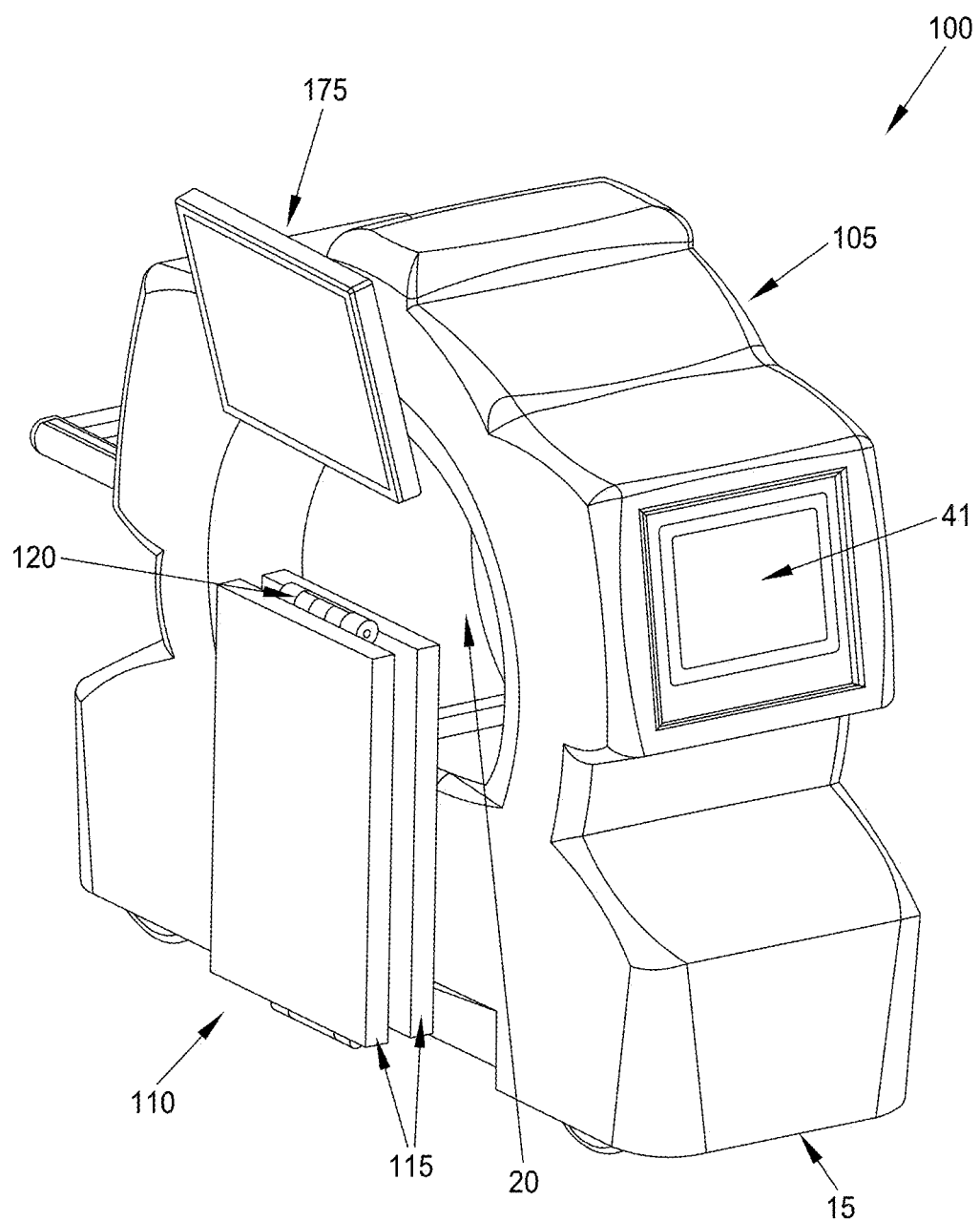
FIGS. 9-13 are schematic views showing a novel mobile CT imaging system formed in accordance with the present invention, the mobile CT imaging system comprising a mobile CT imaging machine with an on-board motorized bed.
Figure 10:
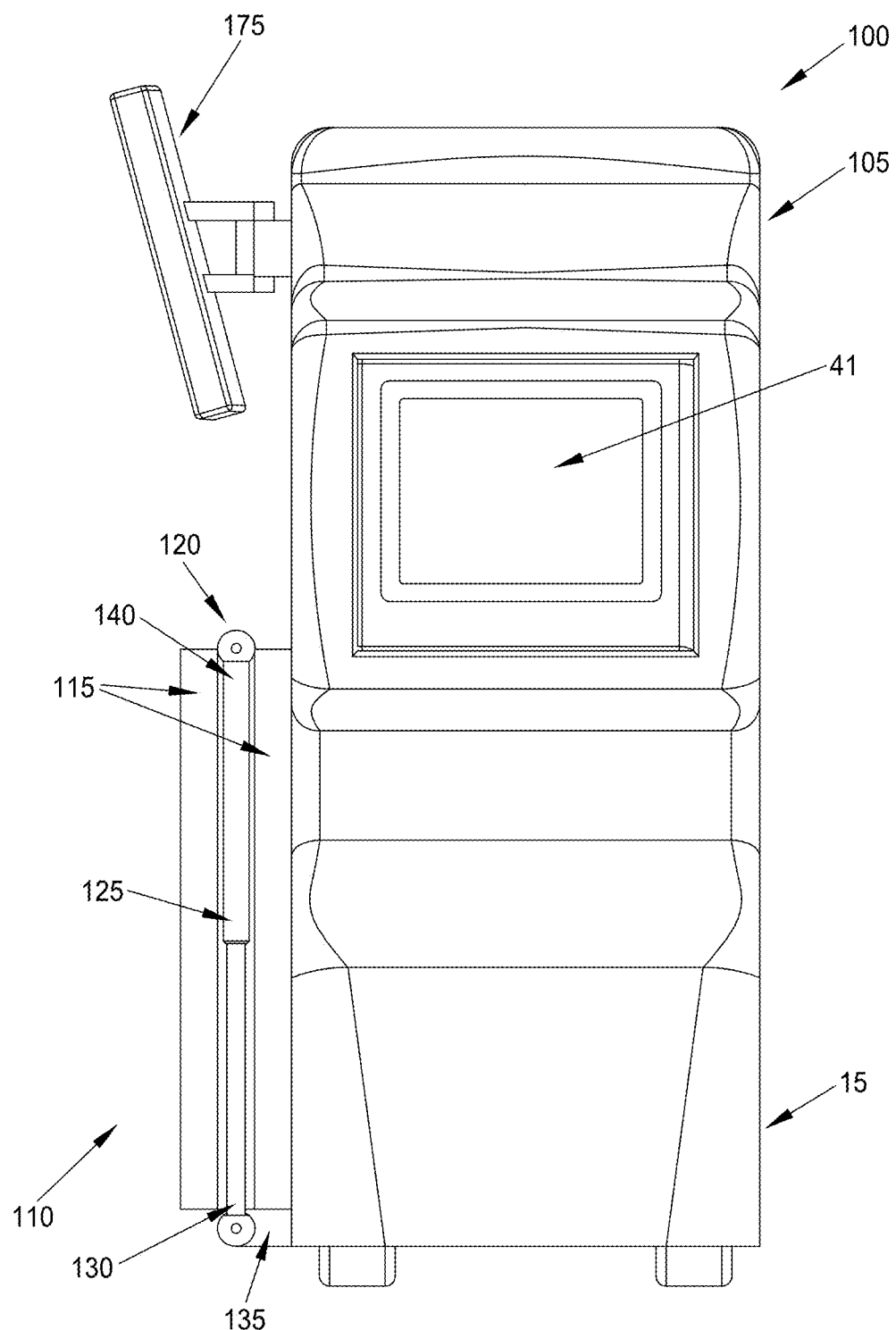
Figure 11:
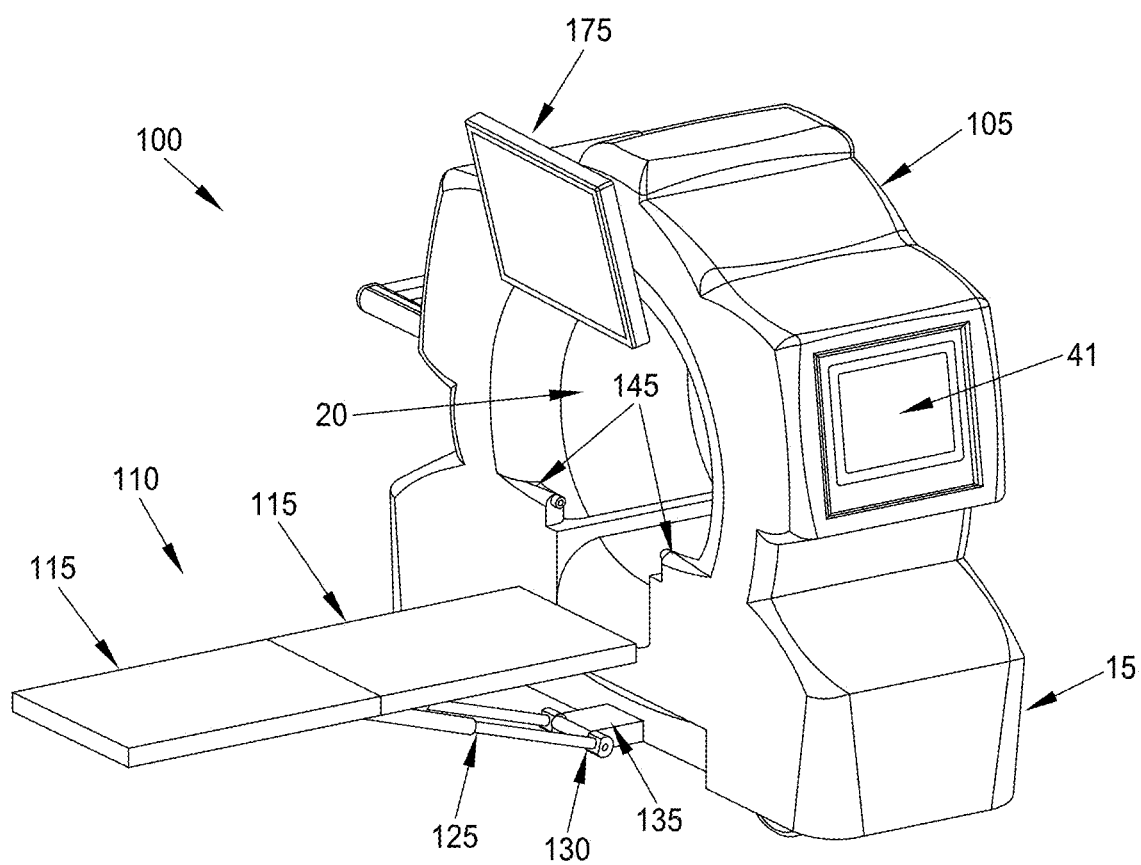
Figure 12:
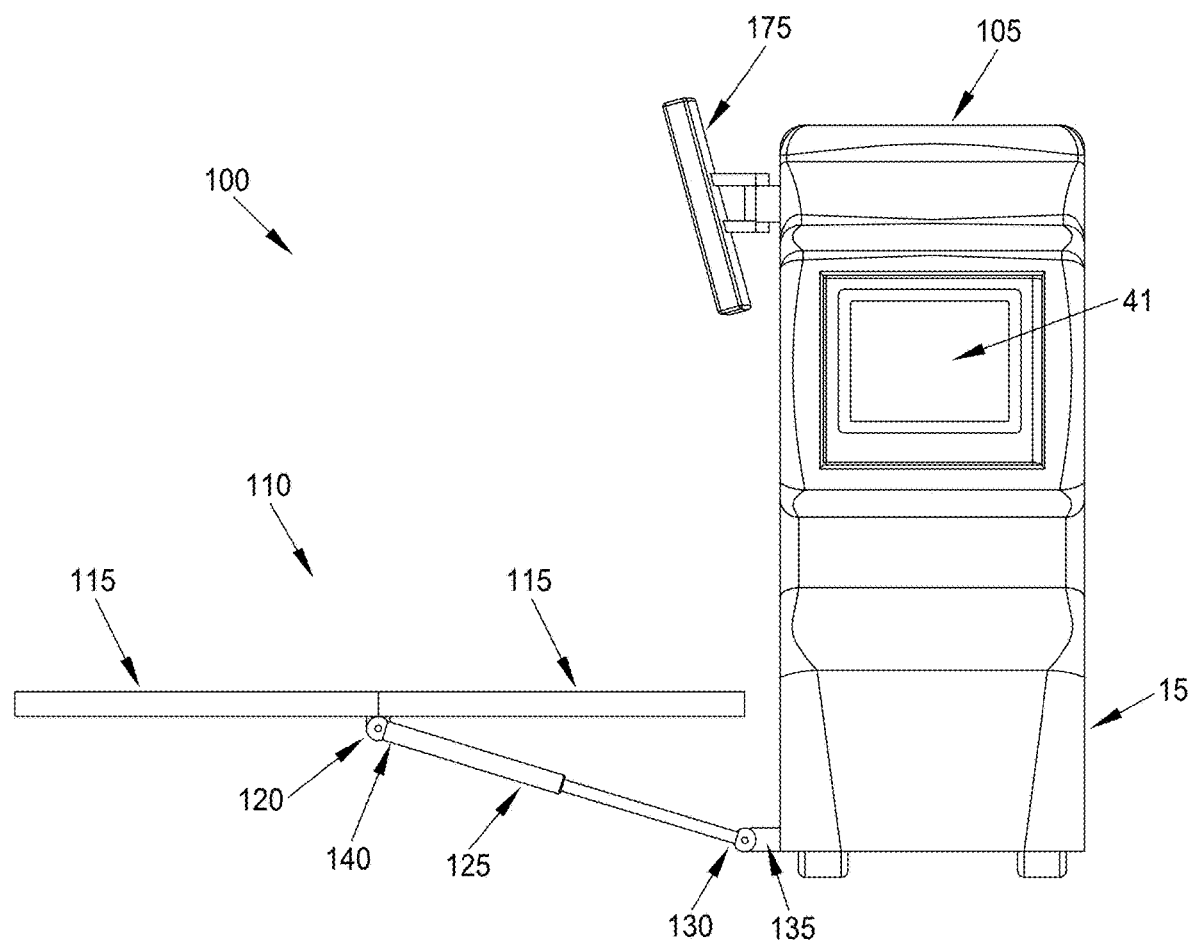
Figure 13:
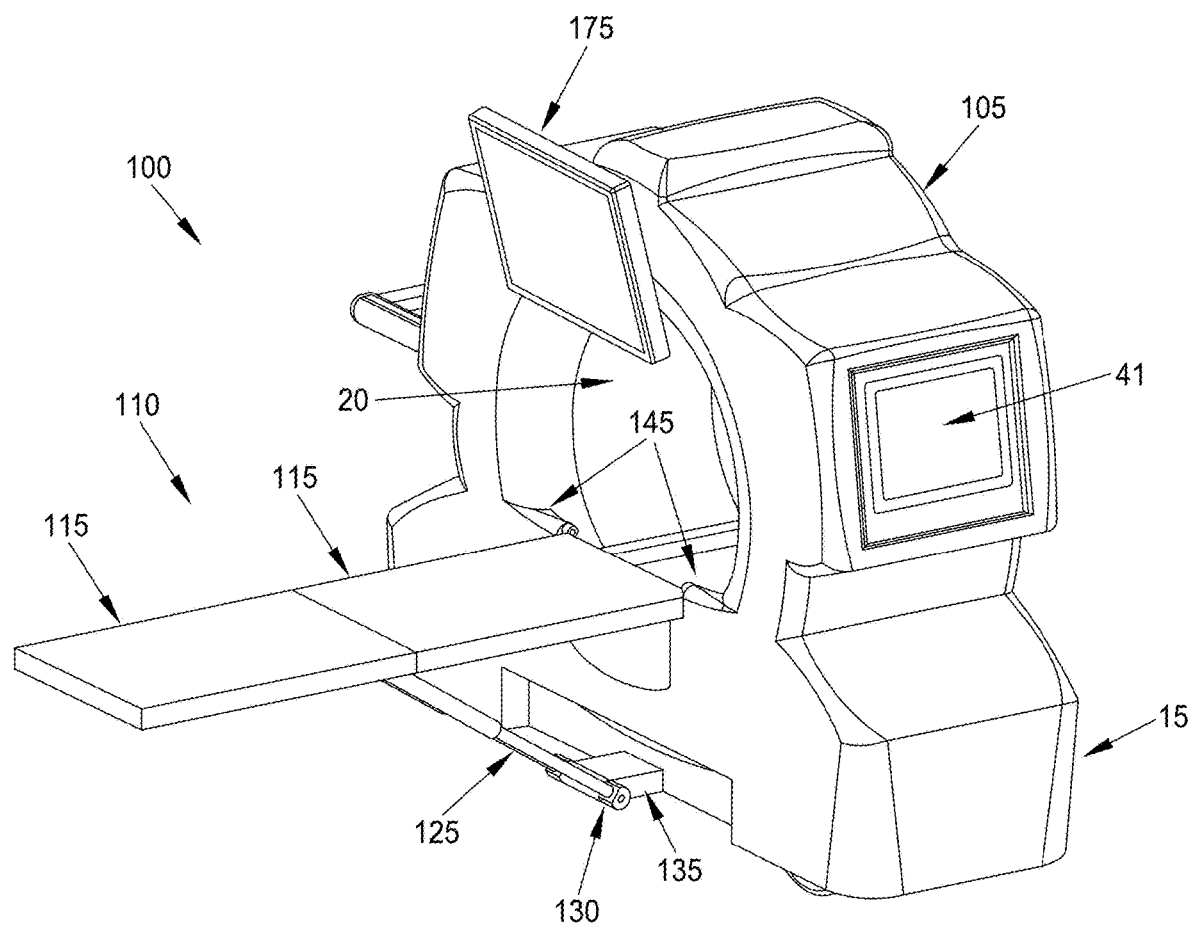
Figure 14:
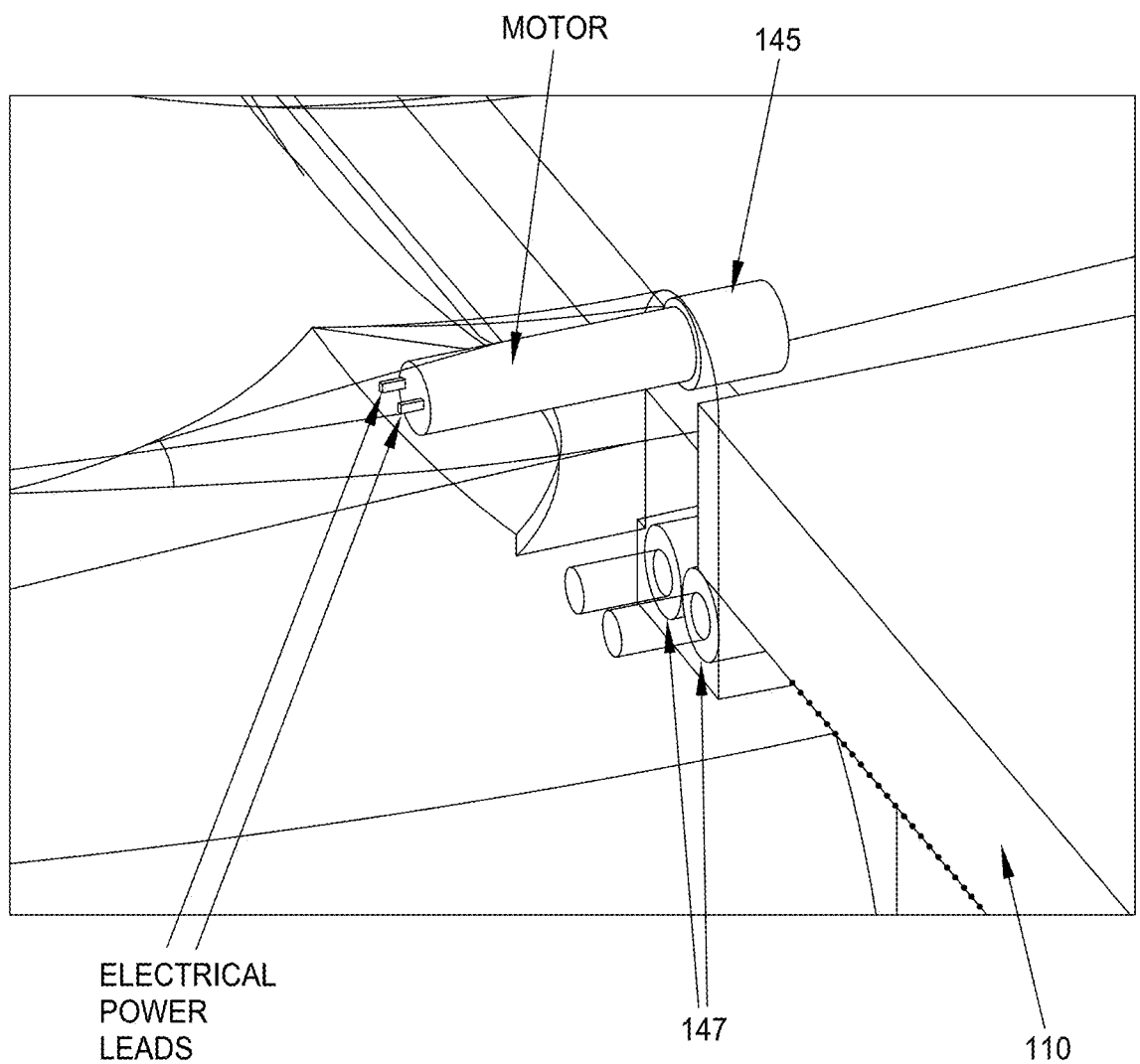
FIGS. 14-17 are schematic views showing details of the powered rollers used to move the on-board motorized bed of the novel mobile CT imaging system of FIGS. 9-13.
Figure 15:
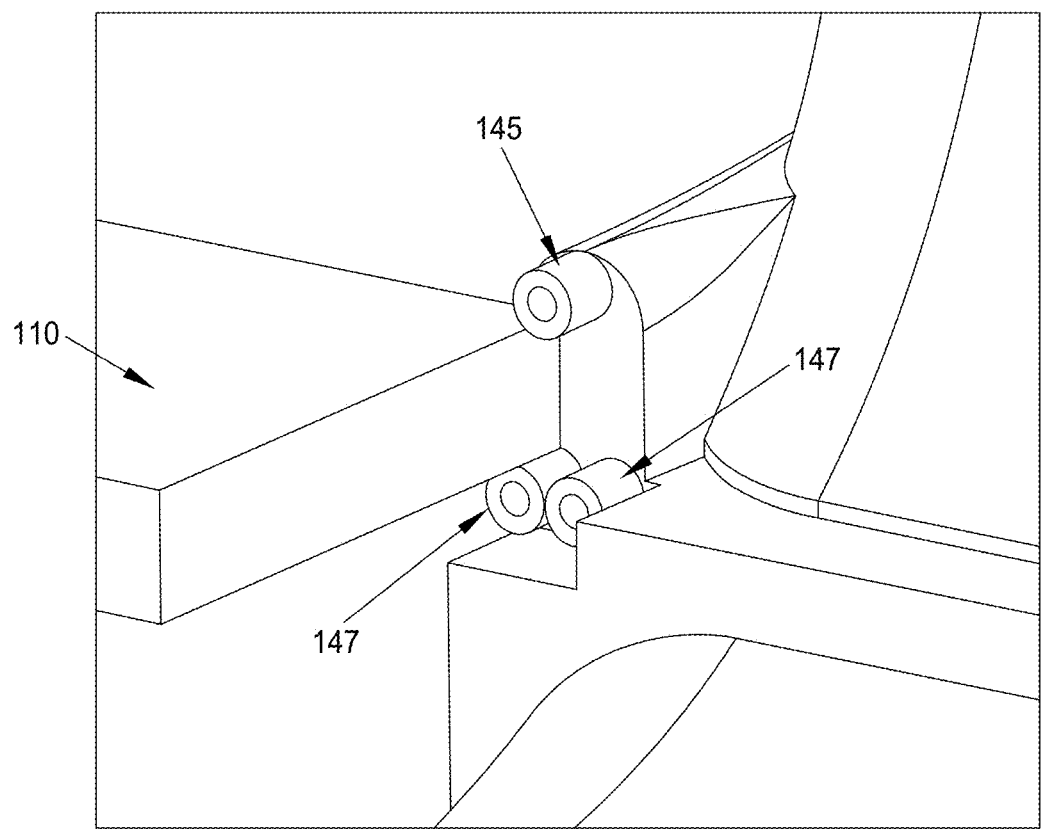
Figure 16:
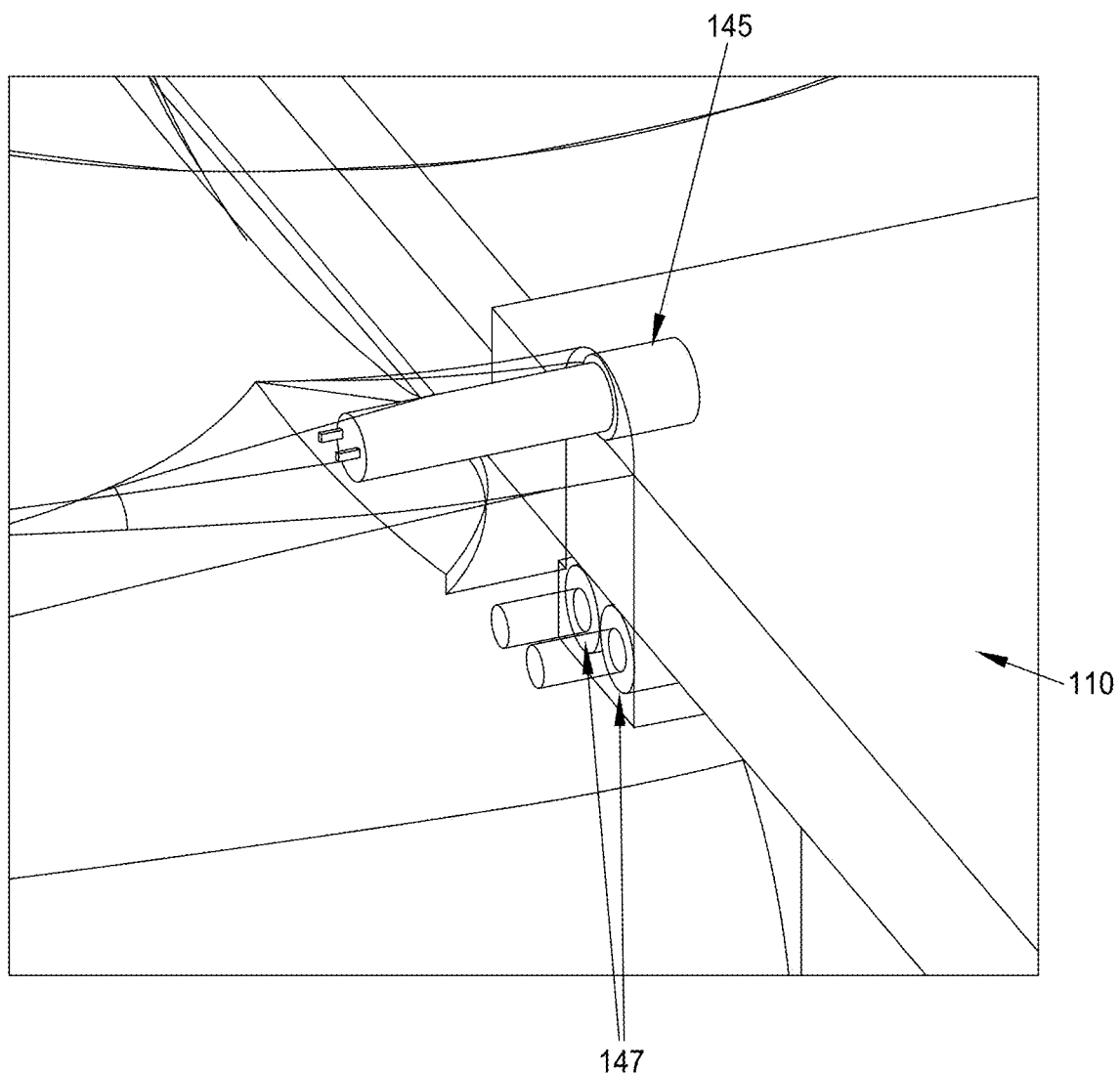
Figure 17:
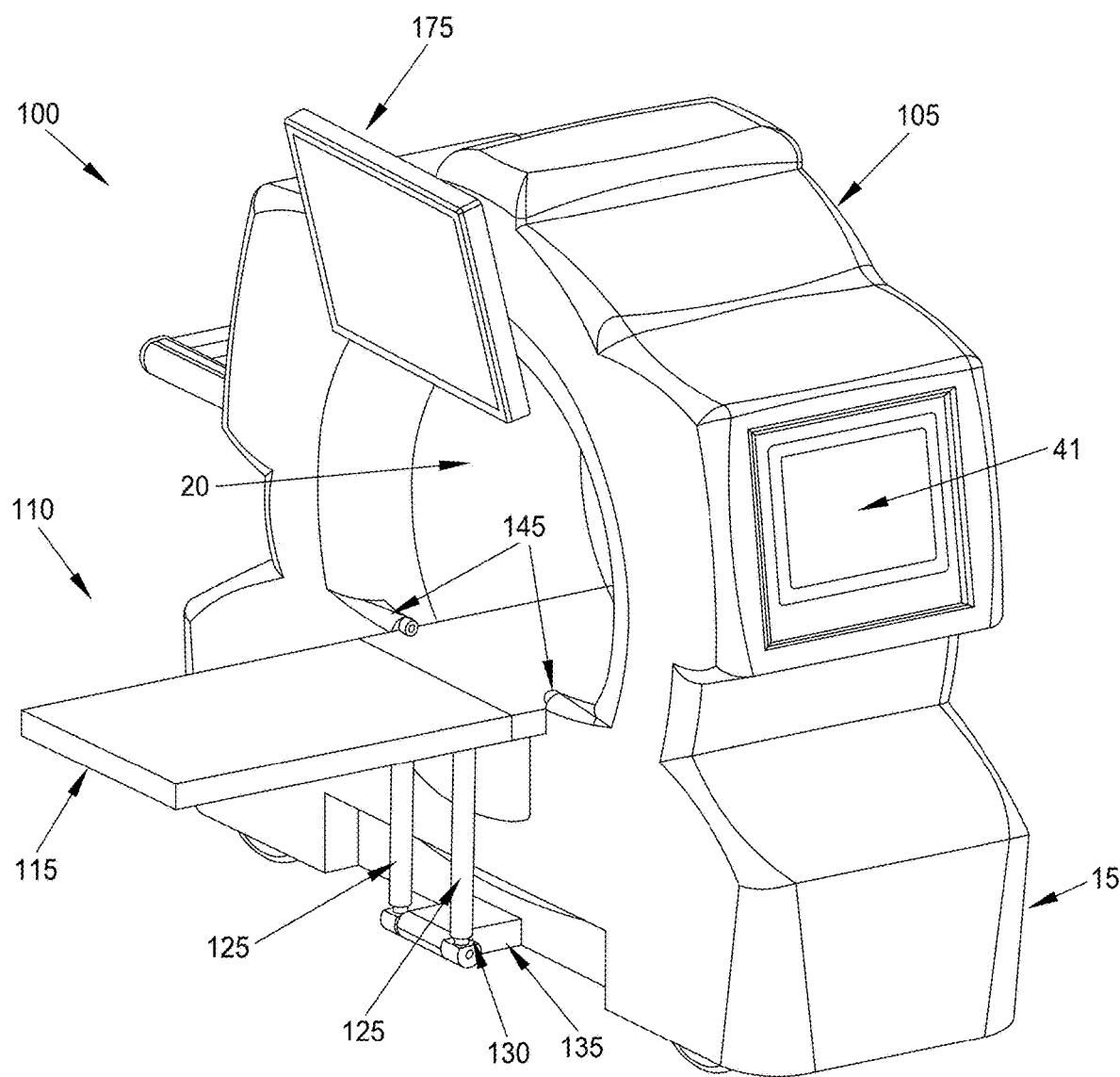

Novel Mobile CT Imaging System Comprising a Mobile CT Imaging Machine with an On-Board Motorized Bed Looking first at FIGS. 9-13, there is shown a novel mobile CT imaging system 100 comprising a mobile CT imaging machine 105 comprising an on-board motorized bed 110.

Novel mobile CT imaging machine 105 may be the aforementioned mobile CT imaging machine 5B (i.e., where free-rolling castors 62 are used to move the system quickly between locations, and centipede belt drives 63 are used to move the machine during scanning); or novel mobile CT imaging machine 105 may be the aforementioned mobile CT imaging machine 5C (i.e., where powered mecanum wheels 70 (also known as "omni" wheels or "ilon" wheels) are used to move the machine quickly between locations, and powered wheels 63C are used to move the machine during scanning); or novel mobile CT imaging machine 105 may be the aforementioned mobile CT imaging machine 5D (i.e., where so-called "Liddiard" wheels 76 are used to move the machine both quickly between locations and during scanning); or novel mobile CT imaging machine 105 may be any other mobile CT imaging machine capable of moving between locations before and/or after scanning.

On-board motorized bed 110 is movably (e.g., pivotally) mounted to mobile CT imaging machine 105. More particularly, in a preferred form of the invention, on-board motorized bed 110 is pivotally mounted to mobile CT imaging machine 105 such that on-board motorized bed 110 is capable of assuming: (i) a first "folded" configuration (which also may be referred to herein as a "transport" configuration) (see FIGS. 9 and 10) in which on-board motorized bed 110 is folded and sits close to the body of mobile CT imaging machine 105, whereby to facilitate movement of mobile CT imaging system 100 within a healthcare environment, and (ii) a second "unfolded" configuration (which also may be referred to herein as a "scanning" configuration) (see FIGS. 11-13) in which on-board motorized bed 110 is unfolded and aligned with the center opening 20 of the mobile CT imaging machine 105, whereby to facilitate scanning of a patient lying on on-board motorized bed 110. If desired, on-board motorized bed 110 may be locked to mobile CT imaging machine 105 when the on-board motorized bed 110 is in its first, folded configuration.

Furthermore, if desired, on-board motorized bed 110 may include powered systems for moving on-board motorized bed 110 between its first "folded" configuration and its second "unfolded" configuration, or on-board motorized bed 110 may include manual systems for moving on-board motorized bed 110 between its first "folded" configuration and its second "unfolded" configuration.

In one preferred form of the invention, on-board motorized bed 110 comprises two patient supports 115 which are pivotally connected to one another at a hinge 120. On-board motorized bed 110 is movably mounted to mobile CT imaging machine 105 by means of telescoping arms 125 which connect patient supports 115 to the base of mobile CT imaging machine 105, as will hereinafter be discussed in further detail. More particularly, telescoping arms 125 comprise a first end 130 pivotally mounted to a mount 135 attached to base 15 of mobile CT imaging machine 105, and a second end 140 which is pivotally mounted to hinge 120. In this way, retracting telescoping arms 125 causes on-board motorized bed 110 to assume its first "folded" configuration, and extending telescoping arms 125 causes on-board motorized bed 110 to assume its second "unfolded" configuration.

Figure 18:
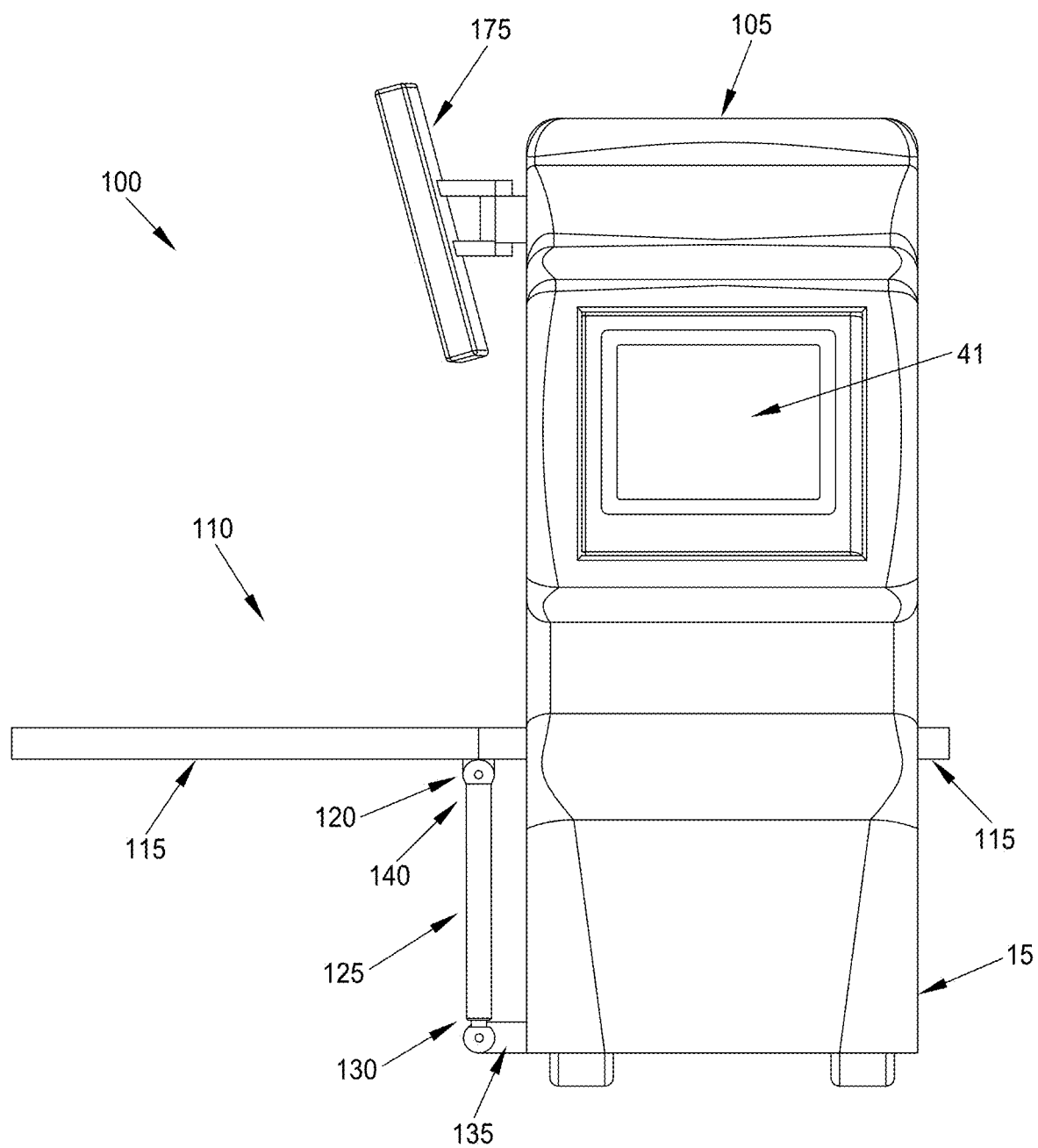
FIG. 18 is a schematic view showing the on-board motorized bed of novel mobile CT imaging system of the present invention in a scanning configuration.

As seen in FIGS. 13-17, mobile CT imaging machine 105 is preferably configured with (i) powered rollers 145 which, when on-board motorized bed 110 is in its second "unfolded" configuration, grip on-board motorized bed 110 and advance on-board motorized bed 110 into, and out of, the center opening 20 of mobile CT imaging machine 105 during scanning of the patient, and (ii) roller conveyors 147 (FIGS. 14-16) which, when on-board motorized bed 110 is in its second "unfolded" configuration, provide a smooth path for on-board motorized bed 110 to move into, and out of, the center opening 20 of mobile CT imaging machine 105 during scanning of the patient. More particularly, powered rollers 145 are configured to rotate in a first direction in order to advance on-board motorized bed 110 into center opening 20 of mobile CT imaging machine 105, whereby to facilitate scanning of a patient (or object) disposed on top of on-board motorized bed 110. As on-board motorized bed 110 is drawn into (and through) center opening 20 of mobile CT imaging machine 105, telescoping arms 125 are configured to pivot relative to on-board motorized bed 110 (e.g., at mount 135) and/or are configured to shorten (i.e., retract) as necessary in order to facilitate movement of on-board motorized bed 110 into center opening 20 while keeping on-board motorized bed 110 level. See FIGS. 17 and 18. Powered rollers 145 are configured to rotate in a second, opposite direction in order to retract on-board motorized bed 110 from center opening 20 of mobile CT imaging machine 105, whereby to facilitate removal of the patient (or object) to be scanned from center opening 20. As on-board motorized bed 110 is retracted out of center opening 20 of mobile CT imaging machine 105, telescoping arms 125 are configured to pivot relative to on-board motorized bed 110 (e.g., at mount 135), and/or are configured to lengthen (i.e., extend) as necessary in order to facilitate movement of on-board motorized bed 110 out of center opening 20 while keeping on-board motorized bed 110 level.

Note that the two patient supports 115 of on-board motorized bed 110 comprise a material which is radiolucent to X-rays, so that when a patient (or object) is lying on on-board motorized bed 110 and the on-board motorized bed 110 advances the patient into the center opening 20 of mobile CT imaging machine 105 during scanning, on-board motorized bed 110 does not interfere with CT imaging of the patient.

Thus it will be seen that mobile CT imaging machine 105 differs from the mobile CT imaging systems 5B, 5C and 5D previously discussed, in the sense that with mobile CT imaging machine 105, relative movement between the patient and the CT imaging machine is not effected by movement of the mobile CT imaging machine relative to the patient, but rather, it is effected by movement of on-board motorized bed 110 relative to mobile CT imaging machine 105 (i.e., movement of on-board motorized bed 110 into or out of center opening 20).

Figure 19:
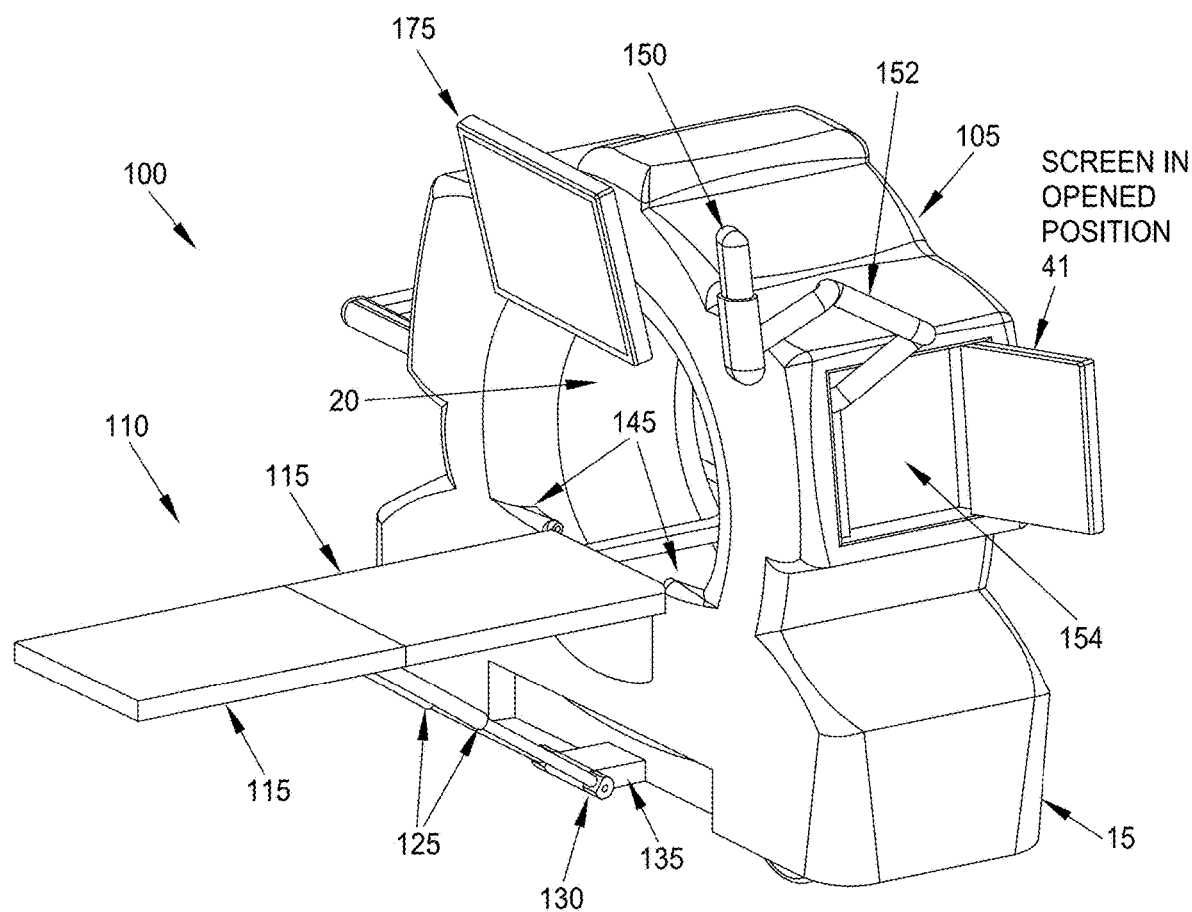
FIG. 19 is a schematic view showing how the novel mobile CT imaging system of the present invention may further comprise a contrast injector.

If desired, and looking next at FIG. 19, the mobile CT imaging system 100 may include a contrast injector 150 which is movably mounted to mobile CT imaging machine 105 and which travels with the mobile CT imaging system 100 as a unit. In a preferred form of the invention, contrast injector 150 is movably mounted to mobile CT imaging machine 105 via a boom arm 152 comprising a plurality of joints for permitting contrast injector 150 to be positioned as desired. When contrast injector 150 is not being utilized, contrast injector 150 may be stowed in a cabinet 154 formed in torus 10 of mobile CT imaging machine 105. If desired, cabinet 154 may be disposed behind display screen 41 (when provided) such that display screen 41 forms the door of cabinet 154.

Figure 20:
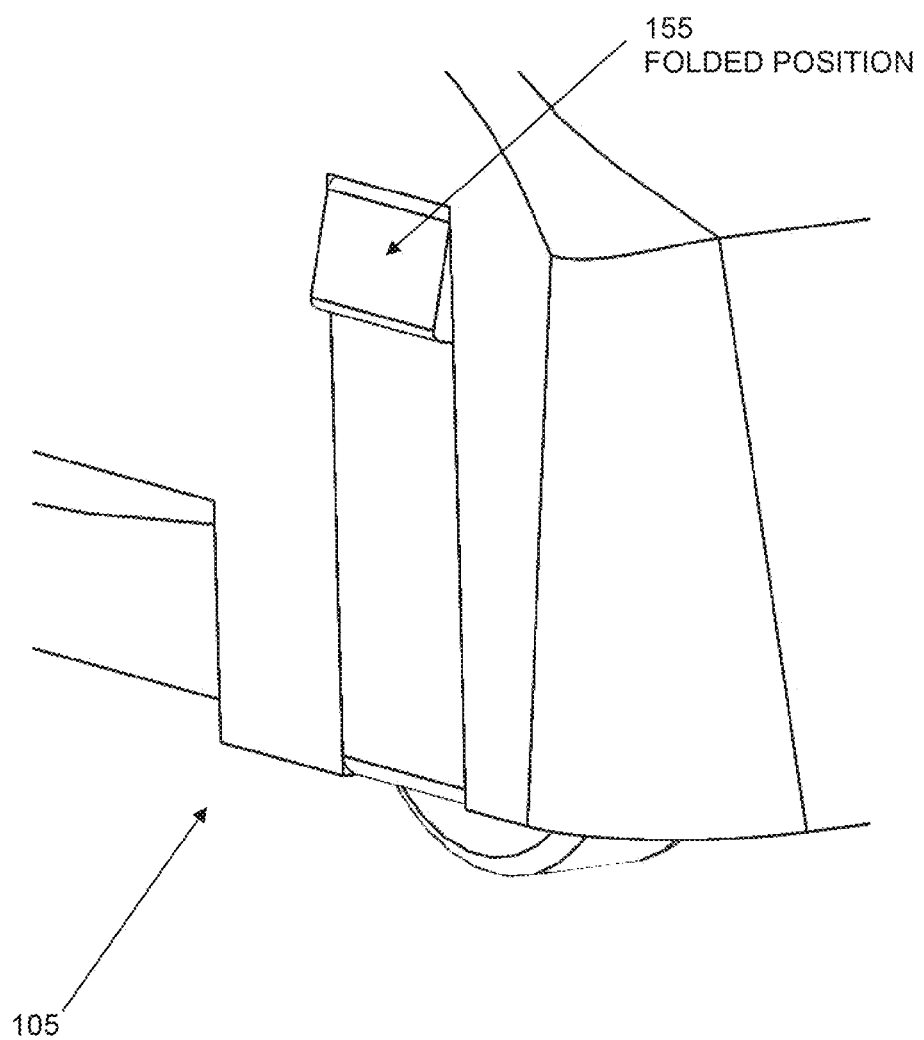
FIGS. 20-22 are schematic views showing deployable feet for stabilizing a mobile CT imaging system when the patient is on a cantilevered bed.
Figure 21:
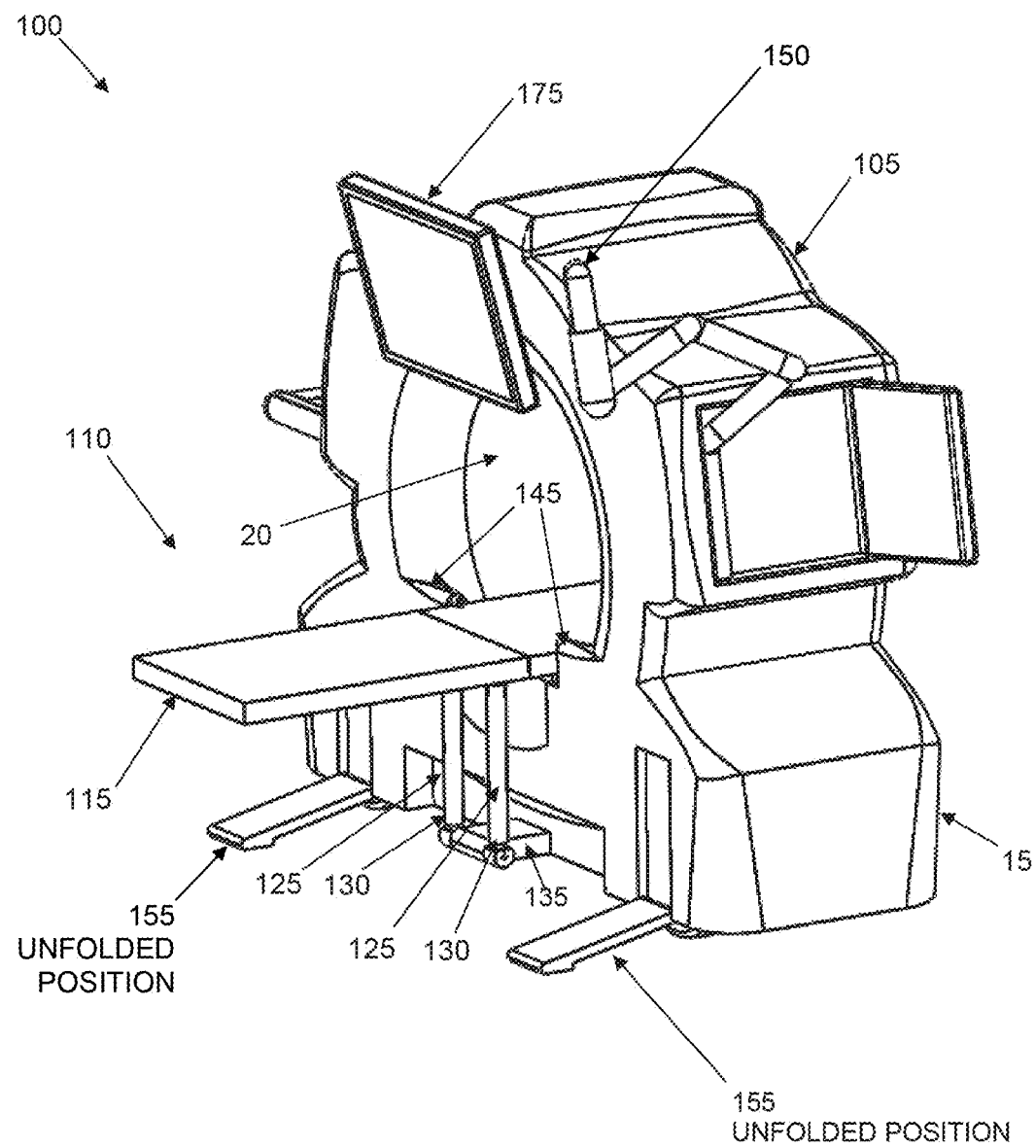
Figure 22:
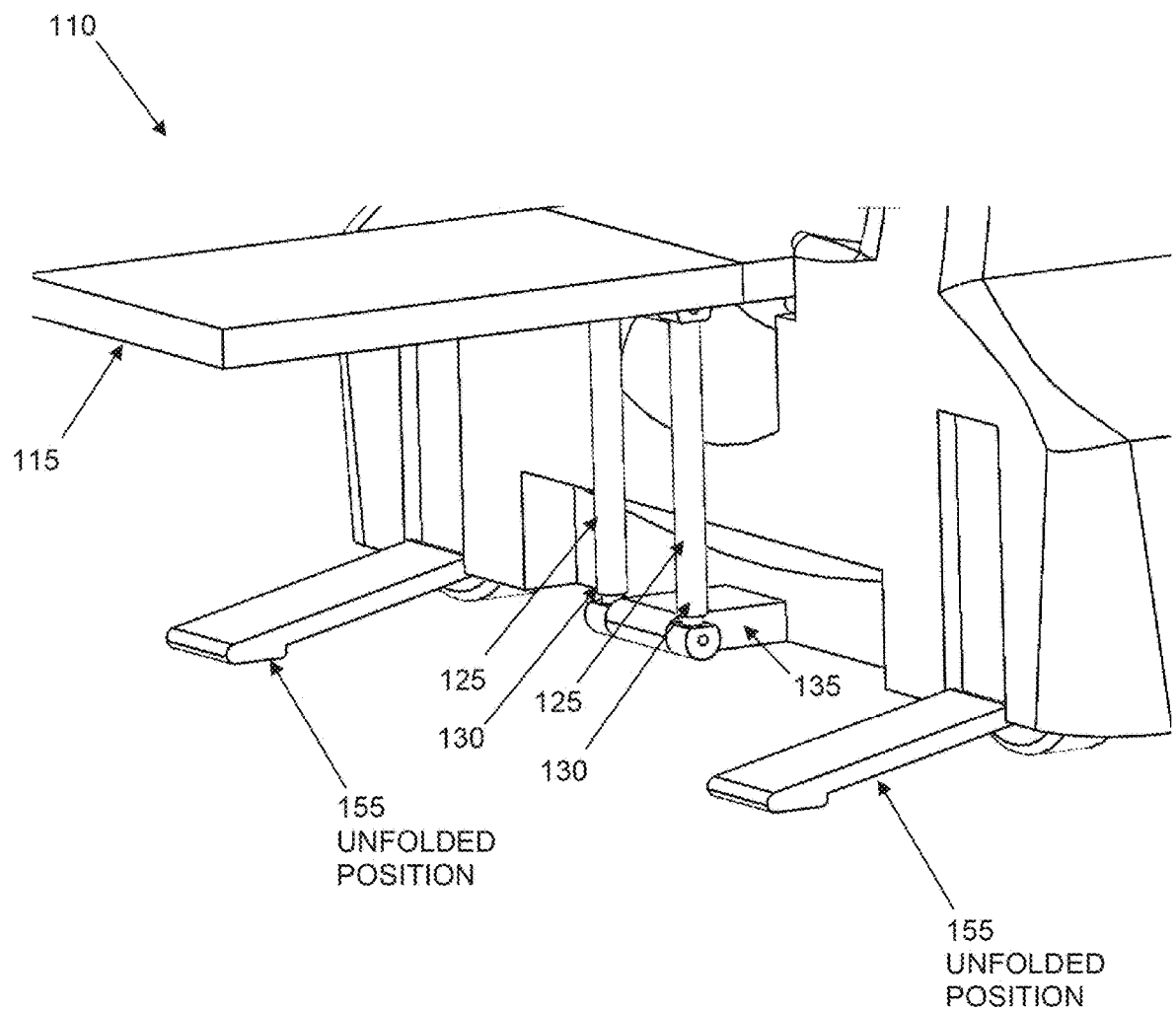

It will be appreciated that when on-board motorized bed 110 is in its second "unfolded" configuration, on-board motorized bed 110 is cantilevered outwardly from mobile CT imaging machine 105. Where mobile CT imaging machine 105 is relatively light-weight, and where a heavy patient (or object) is positioned on on-board motorized bed 110, instability of mobile CT imaging system 100 might occur. In order to prevent this, and looking next at FIGS. 20-22, mobile CT imaging machine 105 may include deployable feet 155 to help stabilize mobile CT imaging system 100 when a patient (or object) is positioned on the cantilevered on-board motorized bed 110.

Deployable feet 155 are movable between a first "folded" configuration in which deployable feet 155 sit close to the body of mobile CT imaging machine 105 (FIG. 20), whereby to facilitate movement of mobile CT imaging system 100 within a healthcare environment, and a second "unfolded" configuration (FIGS. 21 and 22) in which deployable feet 155 extend away from mobile CT imaging machine 105, whereby to provide increased stability for mobile CT imaging system 100.

Novel Mobile CT Imaging System Comprising an On-Board Ultrasound Imager

Figure 23:
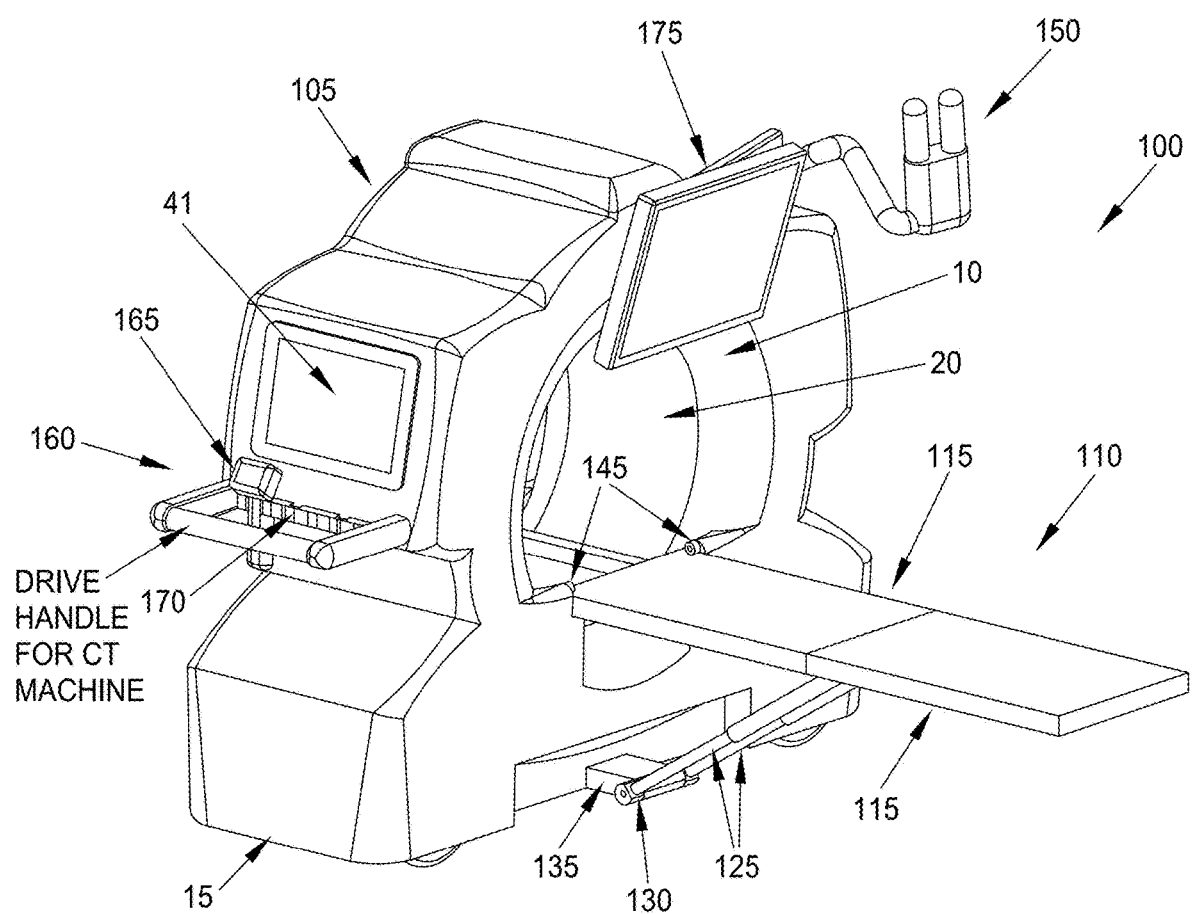
FIG. 23 is a schematic view showing a mobile CT imaging system formed in accordance with the present invention, the mobile CT imaging system comprising a mobile CT imaging machine with an on-board ultrasound imager.

Looking next at FIG. 23, in another form of the invention, novel mobile CT imaging system 100 may comprise a mobile CT imaging machine 105 with an on-board ultrasound imager 160. More particularly, on-board ultrasound imager 160 generally comprises an ultrasound wand 165 which can be stored on a rack 170 on mobile CT imaging machine 105, and an adjustable viewing screen 175 for displaying the images obtained by ultrasound wand 165. More particularly, ultrasound wand 165 comprises an emitter configured to emit sound waves having a frequency appropriate for imaging, and a probe configured to detect reflected sound waves, as will be apparent to one of skill in the art. Ultrasound wand 165 may be wireless, or ultrasound wand 165 may be connected to CT imaging machine 105 via one or more wires. The supporting electronics for on-board ultrasound imager 160 may be housed in the torus 10 and/or base 15 of mobile CT imaging machine 105.

Application to Other Types of Scanning Systems

It should be appreciated that the present invention is not limited to use in medical applications or, indeed, to use with CT machines. Thus, for example, the present invention may be used in connection with mobile CT machines used for non-medical applications, e.g., with mobile CT machines used to scan inanimate objects. Furthermore, the present invention may be used with non-CT-type mobile scanning systems. Thus, for example, the present invention may be used in conjunction with mobile SPECT machines, mobile MRI machines, mobile PET machines, mobile X-ray machines, etc., i.e., wherever the mobile scanning machine may require close tracking to a scan path.

MODIFICATIONS

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. An imaging system for imaging an object, the imaging system comprising:
   an imaging unit comprising a housing having a center opening for receiving the object to be imaged;
   a patient support for supporting the object to be imaged, wherein the patient support comprises a first portion and a second portion, wherein the first portion is pivotally connected to the second portion at a hinge point;
   at least one telescoping arm comprising a first end pivotally mounted to the hinge point of the patient support and a second end pivotally mounted to the imaging unit, wherein the patient support is configured to pivot between (i) a first, folded configuration in which the first and second portions of the patient support are folded at the hinge point and disposed perpendicular to the center opening of the imaging unit, whereby to facilitate transport of the imaging unit, and (ii) a second, unfolded configuration in which the first and second portions of the patient support are unfolded at the hinge point and aligned with the center opening of the imaging unit, whereby to facilitate imaging of the object on the patient support; and
   a plurality of powered rollers configured to rotate in a first direction for advancing the patient support into the center opening of the housing and a second direction for advancing the patient support out of the center opening of the housing;
   wherein the at least one telescoping arm is configured to pivot relative to the patient support so that the patient support remains level as the patient support moves into, and out of, the center opening of the housing.

2. The imaging system according to claim 1 further comprising a powered system for moving the patient support between the folded configuration and the unfolded configuration.

3. The imaging system according to claim 1 further comprising a plurality of roller conveyors for stabilizing the patient support while the patient support is advanced into, and out of, the center opening of the housing.

4. The imaging system according to claim 1 further comprising at least one deployable foot for stabilizing the imaging system.

5. The imaging system according to claim 4 wherein the at least one deployable foot is pivotally mounted to the housing, whereby to be capable of assuming (i) a deployed configuration in which the at least one deployable foot engages a floor surface upon which the imaging system is disposed, and (ii) a storage configuration in which the at least one deployable foot does not engage the floor surface upon which the imaging system is disposed.

6. The imaging system according to claim 1 further comprising a contrast injector mounted to the housing.

7. The imaging system according to claim 6 further comprising a boom arm for movably mounting the contrast injector to the housing.

8. The imaging system according to claim 6 further comprising a cabinet for storing the contrast injector.

9. The imaging system according to claim 1 further comprising an ultrasound imager.

10. The imaging system according to claim 9 wherein the housing comprises a cradle for receiving the ultrasound imager.

11. The imaging system according to claim 9 further comprising a visual display for displaying data obtained by the ultrasound imager.

12. The imaging system according to claim 1 wherein the housing comprises a transport mechanism for moving the imaging unit, wherein the transport mechanism comprises (i) a gross movement mechanism for transporting the imaging unit across room distances, and (ii) a fine movement mechanism for moving the imaging unit precisely, relative to a patient, during scanning.

13. The imaging system according to claim 1 wherein the imaging unit comprises a CT imaging unit.

14. A method for imaging an object, the method comprising:
   providing an imaging system comprising:
      an imaging unit comprising a housing having a center opening for receiving the object to be imaged;
      a patient support for supporting the object to be imaged, wherein the patient support comprises a first portion and a second portion, wherein the first portion is pivotally connected to the second portion at a hinge point;
      at least one telescoping arm comprising a first end pivotally mounted to the hinge point of the patient support and a second end pivotally mounted to the imaging unit, wherein the patient support is configured to pivot between (i) a first, folded configuration in which the first and second portions of the patient support are folded at the hinge point and disposed perpendicular to the center opening of the imaging unit, whereby to facilitate transport of the imaging unit, and (ii) a second, unfolded configuration in which the first and second portions of the patient support are unfolded at the hinge point and aligned with the center opening of the imaging unit, whereby to facilitate imaging of the object on the patient support; and
      a plurality of powered rollers configured to rotate in a first direction for advancing the patient support into the center opening of the housing and a second direction for advancing the patient support out of the center opening of the housing;

positioning the patient support in the second, unfolded configuration;

positioning the object on the patient support while the patient support is in the second, unfolded configuration;

moving the object into the central opening, wherein the at least one telescoping arm is configured to pivot relative to the patient support so that the patient support remains level as the patient support moves into the center opening of the housing; and imaging the object in the central opening.

15. The method according to claim 14 further comprising positioning the patient support in the second, unfolded configuration and transporting the imaging system.

* * * * *